United States Patent
Nhan et al.

(10) Patent No.: US 12,116,706 B2
(45) Date of Patent: *Oct. 15, 2024

(54) PROCESS FOR MAKING THREE-DIMENSIONAL FOAM-LAID NONWOVENS

(71) Applicant: KIMBERLY-CLARK WORLDWIDE, INC., Neenah, WI (US)

(72) Inventors: Davis Dang H. Nhan, Menasha, WI (US); Cathleen M. Uttecht, Menasha, WI (US); Lori A. Eslinger, Appleton, WI (US); Neil T. Scholl, Neenah, WI (US); Jian Qin, Appleton, WI (US); Charles W. Colman, Marietta, GA (US); Deborah J. Calewarts, Winneconne, WI (US); Vasily A Topolkaraev, Appleton, WI (US); Antonio J. Carrillo Ojeda, Appleton, WI (US)

(73) Assignee: KIMBERLY-CLARK WORLDWIDE, INC., Neenah, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 18/240,591

(22) Filed: Aug. 31, 2023

(65) Prior Publication Data
US 2024/0060222 A1    Feb. 22, 2024

Related U.S. Application Data

(63) Continuation of application No. 17/696,071, filed on Mar. 16, 2022, now Pat. No. 11,788,221, which is a
(Continued)

(51) Int. Cl.
*D04H 1/541* (2012.01)
*A61F 13/15* (2006.01)
(Continued)

(52) U.S. Cl.
CPC ..... *D04H 1/5412* (2020.05); *A61F 13/15577* (2013.01); *A61F 13/51104* (2013.01);
(Continued)

(58) Field of Classification Search
CPC .... D04H 1/5412; D04H 1/43916; D04H 1/68; D04H 1/76; D04H 1/732; D04H 1/558;
(Continued)

(56) References Cited

U.S. PATENT DOCUMENTS

| | | |
|---|---|---|
| 2,105,711 A | 1/1938 | Weathered |
| 2,791,523 A | 5/1957 | Schoen |

(Continued)

FOREIGN PATENT DOCUMENTS

| | | |
|---|---|---|
| AT | 517303 A1 | 12/2016 |
| AT | 519414 A2 | 6/2018 |

(Continued)

OTHER PUBLICATIONS

Kalebek, Nazan Avcioglu et al., "Fiber Selection for the Production of Nonwovens", Intech, 2016, https://www.intechopen.com/books/non-woven-fabrics/fiber-selection-for-the-production-of-nonwovens.

*Primary Examiner* — Jose A Fortuna
(74) *Attorney, Agent, or Firm* — KIMBERLY-CLARK WORLDWIDE, INC.

(57) ABSTRACT

A method for making a high topography nonwoven substrate includes generating a foam including water and synthetic binder fibers; depositing the foam on a planar surface; disposing a template form on the foam opposite the planar surface to create a foam/form assembly; heating the foam/form assembly to dry the foam and bind the synthetic binder fibers; and removing the template from the substrate after heating the foam/form assembly, wherein the substrate includes a planar base layer having an X-Y surface and a backside surface opposite the X-Y surface; and a plurality of
(Continued)

projection elements integral with and protruding in a Z-direction from the X-Y surface, wherein the projection elements are distributed in both the X- and Y-directions, and wherein the density of a projection element is the same as the density of the base layer.

20 Claims, 5 Drawing Sheets

Related U.S. Application Data continuation of application No. 17/262,385, filed as application No. PCT/US2018/043662 on Jul. 25, 2018, now Pat. No. 11,313,061.

(51) Int. Cl.
*A61F 13/511* (2006.01)
*D04H 1/4391* (2012.01)
*D04H 1/68* (2012.01)
*D04H 1/76* (2012.01)
*D21H 13/10* (2006.01)
*D21H 21/24* (2006.01)

(52) U.S. Cl.
CPC ........... *D04H 1/43916* (2020.05); *D04H 1/68* (2013.01); *D04H 1/76* (2013.01); *D21H 13/10* (2013.01); *D21H 21/24* (2013.01); *A61F 2013/15934* (2013.01); *A61F 2013/51134* (2013.01)

(58) Field of Classification Search
CPC ...... D04H 1/541; D04H 13/001; D04H 13/00; A61F 13/15577; A61F 13/51104; A61F 2013/15934; A61F 2013/51134; A61F 13/51121; A61F 13/494; A61F 13/513; A61F 2013/5113; D21H 13/10; D21H 13/12; D21H 13/14; D21H 13/16; D21H 13/18; D21H 13/20; D21H 13/22; D21H 13/24; D21H 13/26; D21H 21/24
See application file for complete search history.

(56) References Cited

U.S. PATENT DOCUMENTS

| | | |
|---|---|---|
| 3,007,840 A | 11/1961 | Wilcox |
| 3,506,538 A | 4/1970 | Friedberg et al. |
| 3,542,640 A | 11/1970 | Friedberg et al. |
| 3,544,417 A | 12/1970 | Corzine |
| 3,546,060 A | 12/1970 | Hoppe et al. |
| 3,615,975 A | 10/1971 | Gillern et al. |
| 3,716,449 A | 2/1973 | Gatward et al. |
| 3,741,854 A | 6/1973 | De Gioia |
| 3,765,810 A | 10/1973 | Smarook |
| 3,798,122 A | 3/1974 | Appel |
| 3,837,999 A | 9/1974 | Chung |
| 3,839,142 A | 10/1974 | Clarke et al. |
| 3,871,952 A | 3/1975 | Robertson |
| 3,929,560 A | 12/1975 | Holik et al. |
| 3,938,782 A | 2/1976 | Robertson |
| 3,966,540 A | 6/1976 | Selander et al. |
| 4,007,083 A | 2/1977 | Ring et al. |
| 4,049,491 A | 9/1977 | Brandon et al. |
| 4,062,721 A | 12/1977 | Guyer et al. |
| 4,123,787 A | 10/1978 | Leclerc du Sablon et al. |
| 4,200,488 A | 4/1980 | Brandon et al. |
| 4,285,767 A | 8/1981 | Page |
| 4,288,475 A | 9/1981 | Meeker |
| 4,299,655 A | 11/1981 | Skaugen |
| 4,394,930 A | 7/1983 | Korpman |
| 4,415,388 A | 11/1983 | Korpman |
| 4,443,232 A | 4/1984 | Kaiser |
| 4,443,297 A | 4/1984 | Cheshire et al. |
| 4,443,299 A | 4/1984 | Cheshire et al. |
| 4,464,224 A | 8/1984 | Matolcsy |
| 4,478,615 A | 10/1984 | Kaiser |
| 4,498,956 A | 2/1985 | Cheshire et al. |
| 4,543,156 A | 9/1985 | Cheshire et al. |
| 4,613,627 A | 9/1986 | Sherman et al. |
| 4,637,949 A | 1/1987 | Manning et al. |
| 4,655,950 A | 4/1987 | Michalek |
| 4,686,006 A | 8/1987 | Cheshire et al. |
| 4,734,321 A | 3/1988 | Radvan et al. |
| 4,764,253 A | 8/1988 | Cheshire et al. |
| 4,773,408 A | 9/1988 | Cilento et al. |
| 4,773,409 A | 9/1988 | Cilento et al. |
| 4,778,477 A | 10/1988 | Lauchenauer |
| 4,883,478 A | 11/1989 | Lerailler et al. |
| 4,939,030 A | 7/1990 | Tsuji et al. |
| 4,944,843 A | 7/1990 | Wallace et al. |
| 4,948,007 A | 8/1990 | Berg et al. |
| 4,952,448 A | 8/1990 | Bullock et al. |
| 4,969,975 A | 11/1990 | Biggs et al. |
| 4,973,382 A | 11/1990 | Kinn et al. |
| 4,985,467 A | 1/1991 | Kelly et al. |
| 5,006,373 A | 4/1991 | Woodmansee et al. |
| 5,008,306 A | 4/1991 | Goguelin |
| 5,013,405 A | 5/1991 | Izard |
| 5,064,653 A | 11/1991 | Sessions et al. |
| 5,065,752 A | 11/1991 | Sessions et al. |
| 5,073,416 A | 12/1991 | Avakian et al. |
| 5,098,778 A | 3/1992 | Minnick |
| 5,102,501 A | 4/1992 | Eber et al. |
| 5,134,959 A | 8/1992 | Woodmansee et al. |
| 5,137,551 A | 8/1992 | Ahrens et al. |
| 5,147,345 A | 9/1992 | Young et al. |
| 5,153,058 A | 10/1992 | Hall et al. |
| 5,164,045 A | 11/1992 | Awofeso et al. |
| 5,178,729 A | 1/1993 | Janda |
| 5,196,090 A | 3/1993 | Corbellini et al. |
| 5,200,035 A | 4/1993 | Bhat et al. |
| 5,227,023 A | 7/1993 | Pounder et al. |
| 5,238,534 A | 8/1993 | Manning et al. |
| 5,260,017 A | 11/1993 | Giles |
| 5,260,345 A | 11/1993 | DesMarais et al. |
| 5,268,224 A | 12/1993 | DesMarais et al. |
| 5,300,565 A | 4/1994 | Berg et al. |
| 5,308,565 A | 5/1994 | Weber et al. |
| 5,318,554 A | 6/1994 | Young et al. |
| 5,328,935 A | 7/1994 | Van Phan et al. |
| 5,330,822 A | 7/1994 | Berg et al. |
| 5,331,015 A | 7/1994 | DesMarais et al. |
| 5,338,766 A | 8/1994 | Phan et al. |
| 5,344,866 A | 9/1994 | Hall |
| 5,348,453 A | 9/1994 | Baran et al. |
| 5,369,007 A | 11/1994 | Kidwell |
| 5,372,766 A | 12/1994 | Roe |
| 5,384,179 A | 1/1995 | Roe et al. |
| 5,387,207 A | 2/1995 | Dyer et al. |
| 5,393,379 A | 2/1995 | Parrinello |
| 5,397,316 A | 3/1995 | LaVon et al. |
| 5,397,626 A | 3/1995 | Berg et al. |
| 5,409,572 A | 4/1995 | Kershaw et al. |
| 5,428,076 A | 6/1995 | Roe |
| 5,434,194 A | 7/1995 | Fujimoto et al. |
| 5,451,452 A | 9/1995 | Phan et al. |
| 5,468,437 A | 11/1995 | Hall |
| 5,506,046 A | 4/1996 | Andersen et al. |
| 5,506,277 A | 4/1996 | Griesbach |
| 5,508,072 A | 4/1996 | Andersen et al. |
| 5,533,244 A | 7/1996 | Wadzinski |
| 5,536,264 A | 7/1996 | Hsueh et al. |
| 5,545,450 A | 8/1996 | Andersen et al. |
| 5,549,589 A | 8/1996 | Horney et al. |
| 5,550,167 A | 8/1996 | DesMarais |
| 5,560,878 A | 10/1996 | Dragoo et al. |
| 5,563,179 A | 10/1996 | Stone et al. |
| D375,633 S | 11/1996 | Spanagel et al. |
| 5,571,849 A | 11/1996 | DesMarais |
| 5,580,624 A | 12/1996 | Andersen et al. |
| 5,582,670 A | 12/1996 | Andersen et al. |

(56) References Cited

U.S. PATENT DOCUMENTS

| | | |
|---|---|---|
| 5,585,432 A | 12/1996 | Lee et al. |
| 5,586,842 A | 12/1996 | Bae et al. |
| 5,599,334 A | 2/1997 | Johnston et al. |
| 5,612,385 A | 3/1997 | Ceaser et al. |
| D378,876 S | 4/1997 | Spanagel et al. |
| 5,618,341 A | 4/1997 | Andersen et al. |
| 5,624,971 A | 4/1997 | Wilson |
| 5,626,857 A | 5/1997 | Thimineur et al. |
| 5,631,053 A | 5/1997 | Andersen et al. |
| 5,632,737 A | 5/1997 | Stone et al. |
| 5,633,291 A | 5/1997 | Dyer et al. |
| 5,649,409 A | 7/1997 | Gujer et al. |
| 5,650,222 A | 7/1997 | DesMarais et al. |
| D381,810 S | 8/1997 | Schultz et al. |
| 5,658,603 A | 8/1997 | Andersen et al. |
| 5,660,900 A | 8/1997 | Andersen et al. |
| 5,660,903 A | 8/1997 | Andersen et al. |
| 5,660,904 A | 8/1997 | Andersen et al. |
| 5,662,731 A | 9/1997 | Andersen et al. |
| 5,665,442 A | 9/1997 | Andersen et al. |
| 5,674,917 A | 10/1997 | Wilson |
| 5,679,145 A | 10/1997 | Andersen et al. |
| 5,679,218 A | 10/1997 | Vinson et al. |
| 5,683,772 A | 11/1997 | Andersen et al. |
| 5,691,014 A | 11/1997 | Andersen et al. |
| 5,692,939 A | 12/1997 | DesMarais |
| 5,693,403 A | 12/1997 | Brown et al. |
| 5,695,607 A | 12/1997 | Oriaran et al. |
| 5,702,571 A | 12/1997 | Kamps et al. |
| 5,705,203 A | 1/1998 | Andersen et al. |
| 5,705,238 A | 1/1998 | Andersen et al. |
| 5,705,239 A | 1/1998 | Andersen et al. |
| 5,705,242 A | 1/1998 | Andersen et al. |
| 5,707,474 A | 1/1998 | Andersen et al. |
| 5,707,579 A | 1/1998 | Habelski et al. |
| 5,709,827 A | 1/1998 | Andersen et al. |
| 5,709,913 A | 1/1998 | Andersen et al. |
| D390,363 S | 2/1998 | Baum et al. |
| 5,713,881 A | 2/1998 | Rezai et al. |
| 5,716,563 A | 2/1998 | Winterowd et al. |
| 5,716,675 A | 2/1998 | Andersen et al. |
| 5,719,201 A | 2/1998 | Wilson |
| 5,720,851 A | 2/1998 | Reiner |
| 5,728,743 A | 3/1998 | Dyer et al. |
| 5,736,209 A | 4/1998 | Andersen et al. |
| 5,741,581 A | 4/1998 | DesMarais et al. |
| 5,744,506 A | 4/1998 | Goldman et al. |
| 5,744,509 A | 4/1998 | Wilson et al. |
| 5,753,308 A | 5/1998 | Andersen et al. |
| 5,753,359 A | 5/1998 | Dyer et al. |
| 5,763,499 A | 6/1998 | DesMarais |
| 5,770,634 A | 6/1998 | Dyer et al. |
| 5,776,388 A | 7/1998 | Andersen et al. |
| 5,783,126 A | 7/1998 | Andersen et al. |
| 5,795,921 A | 8/1998 | Dyer et al. |
| 5,800,416 A | 9/1998 | Seger et al. |
| 5,800,647 A | 9/1998 | Andersen et al. |
| 5,810,961 A | 9/1998 | Andersen et al. |
| 5,817,703 A | 10/1998 | Blair et al. |
| 5,830,305 A | 11/1998 | Andersen et al. |
| 5,843,055 A | 12/1998 | Seger |
| 5,843,544 A | 12/1998 | Andersen et al. |
| 5,849,155 A | 12/1998 | Gasland |
| 5,849,805 A | 12/1998 | Dyer |
| 5,851,634 A | 12/1998 | Andersen et al. |
| 5,851,648 A | 12/1998 | Stone et al. |
| 5,853,402 A | 12/1998 | Faulks et al. |
| 5,863,958 A | 1/1999 | Dyer et al. |
| 5,868,724 A | 2/1999 | Dierckes et al. |
| 5,876,643 A | 3/1999 | Biggs et al. |
| 5,879,722 A | 3/1999 | Andersen et al. |
| 5,882,479 A | 3/1999 | Oriaran et al. |
| 5,899,893 A | 5/1999 | Dyer et al. |
| 5,900,114 A | 5/1999 | Brown et al. |
| 5,904,809 A | 5/1999 | Rokman et al. |
| 5,904,812 A | 5/1999 | Salman et al. |
| 5,908,533 A | 6/1999 | Marinack et al. |
| 5,916,503 A | 6/1999 | Rettenbacher |
| 5,916,928 A | 6/1999 | Sessions et al. |
| 5,919,411 A | 7/1999 | Rezai et al. |
| 5,922,780 A | 7/1999 | Dyer et al. |
| 5,925,299 A | 7/1999 | Dierckes et al. |
| 5,928,741 A | 7/1999 | Andersen et al. |
| 5,948,829 A | 9/1999 | Wallajapet et al. |
| 5,958,186 A | 9/1999 | Holm et al. |
| 5,976,235 A | 11/1999 | Andersen et al. |
| 5,985,434 A | 11/1999 | Qin et al. |
| 6,001,218 A | 12/1999 | Hsu et al. |
| 6,013,293 A | 1/2000 | De Moor |
| 6,013,589 A | 1/2000 | DesMarais et al. |
| 6,017,833 A | 1/2000 | Reiner et al. |
| 6,019,871 A | 2/2000 | Rokman et al. |
| 6,022,615 A | 2/2000 | Rettenbacher |
| 6,027,610 A | 2/2000 | Back et al. |
| 6,030,673 A | 2/2000 | Andersen et al. |
| 6,037,282 A | 3/2000 | Milding et al. |
| D423,232 S | 4/2000 | Reid |
| 6,051,104 A | 4/2000 | Oriaran et al. |
| 6,054,022 A | 4/2000 | Helwig et al. |
| 6,074,527 A | 6/2000 | Hsu et al. |
| 6,077,390 A | 6/2000 | Salman et al. |
| 6,077,590 A | 6/2000 | Archer et al. |
| 6,083,211 A | 7/2000 | DesMarais |
| 6,083,586 A | 7/2000 | Andersen et al. |
| 6,086,718 A | 7/2000 | Carter et al. |
| 6,090,195 A | 7/2000 | Andersen et al. |
| 6,093,359 A | 7/2000 | Gauchel et al. |
| 6,096,809 A | 8/2000 | Lorcks et al. |
| 6,103,060 A | 8/2000 | Munerelle et al. |
| 6,103,063 A | 8/2000 | Oriaran et al. |
| D430,406 S | 9/2000 | Ingalls |
| D430,407 S | 9/2000 | Ingalls |
| D430,734 S | 9/2000 | Bredendick et al. |
| 6,113,740 A | 9/2000 | Oriaran et al. |
| D431,371 S | 10/2000 | Ingalls et al. |
| D431,372 S | 10/2000 | Ingalls et al. |
| 6,133,193 A | 10/2000 | Kajikawa et al. |
| 6,136,153 A | 10/2000 | Rokman et al. |
| 6,136,873 A | 10/2000 | Hahnle et al. |
| 6,153,053 A | 11/2000 | Harper et al. |
| 6,160,028 A | 12/2000 | Dyer |
| 6,162,961 A | 12/2000 | Tanner et al. |
| 6,163,943 A | 12/2000 | Johansson et al. |
| D436,738 S | 1/2001 | Bredendick et al. |
| 6,168,857 B1 | 1/2001 | Andersen et al. |
| 6,174,152 B1 | 1/2001 | Rokman et al. |
| 6,174,929 B1 | 1/2001 | Hähnle et al. |
| D437,119 S | 2/2001 | Jahner et al. |
| D437,120 S | 2/2001 | Jahner et al. |
| D437,489 S | 2/2001 | Jahner et al. |
| D438,017 S | 2/2001 | Reid |
| 6,193,838 B1 | 2/2001 | Oriaran et al. |
| 6,200,404 B1 | 3/2001 | Andersen et al. |
| 6,203,663 B1 | 3/2001 | Kamps et al. |
| 6,207,244 B1 | 3/2001 | Hesch |
| D440,051 S | 4/2001 | Bredendick et al. |
| 6,214,907 B1 | 4/2001 | Tomka |
| 6,231,960 B1 | 5/2001 | Dyer et al. |
| 6,231,970 B1 | 5/2001 | Andersen et al. |
| 6,235,816 B1 | 5/2001 | Lorcks et al. |
| 6,238,518 B1 | 5/2001 | Rokman et al. |
| D443,766 S | 6/2001 | Bredendick et al. |
| 6,243,934 B1 | 6/2001 | Wadzinski |
| 6,245,410 B1 | 6/2001 | Hähnle et al. |
| 6,245,697 B1 | 6/2001 | Conrad et al. |
| 6,248,211 B1 | 6/2001 | Jennings et al. |
| 6,251,207 B1 | 6/2001 | Schultz et al. |
| 6,258,203 B1 | 7/2001 | Rokman et al. |
| 6,261,679 B1 | 7/2001 | Chen et al. |
| 6,274,077 B1 | 8/2001 | Hur et al. |
| 6,280,570 B1 | 8/2001 | Harper et al. |
| 6,287,417 B1 | 9/2001 | Bhat |
| 6,287,422 B1 | 9/2001 | Harper et al. |
| 6,296,736 B1 | 10/2001 | Hsu et al. |

(56) References Cited

U.S. PATENT DOCUMENTS

| | | |
|---|---|---|
| 6,296,929 B1 | 10/2001 | Gentile et al. |
| 6,309,661 B1 | 10/2001 | Haynes et al. |
| 6,355,142 B1 | 3/2002 | Ahrens |
| 6,372,087 B2 | 4/2002 | Harper et al. |
| 6,376,032 B1 | 4/2002 | Clarke et al. |
| 6,387,210 B1 | 5/2002 | Hsu et al. |
| D459,897 S | 7/2002 | Bredendick et al. |
| 6,413,368 B1 | 7/2002 | Dwiggins et al. |
| 6,419,790 B1 | 7/2002 | Leege et al. |
| 6,425,983 B1 | 7/2002 | Marinack et al. |
| 6,432,272 B1 | 8/2002 | Hollenberg et al. |
| 6,436,234 B1 | 8/2002 | Chen et al. |
| 6,440,266 B1 | 8/2002 | George et al. |
| 6,443,258 B1 | 9/2002 | Putt et al. |
| 6,444,088 B2 | 9/2002 | Rökman et al. |
| 6,447,640 B1 | 9/2002 | Watson et al. |
| 6,451,166 B1 | 9/2002 | Marinack et al. |
| 6,455,600 B1 | 9/2002 | Hähnle et al. |
| 6,472,497 B2 | 10/2002 | Loercks et al. |
| 6,500,302 B2 | 12/2002 | Dwiggins et al. |
| 6,503,372 B1 | 1/2003 | Rokman et al. |
| 6,518,479 B1 | 2/2003 | Graef et al. |
| 6,525,240 B1 | 2/2003 | Graef et al. |
| 6,527,913 B1 | 3/2003 | Johnson et al. |
| 6,531,078 B2 | 3/2003 | Laine et al. |
| 6,540,879 B2 | 4/2003 | Marinack et al. |
| 6,544,386 B2 | 4/2003 | Krzysik et al. |
| 6,548,132 B1 | 4/2003 | Clarke et al. |
| 6,562,193 B1 | 5/2003 | Elonen et al. |
| 6,589,634 B2 | 7/2003 | Schultz et al. |
| 6,596,389 B1 | 7/2003 | Hallett et al. |
| 6,600,086 B1 | 7/2003 | Mace et al. |
| 6,603,054 B2 | 8/2003 | Chen et al. |
| 6,613,424 B1 | 9/2003 | Putt et al. |
| 6,616,802 B1 | 9/2003 | Kinsley, Jr. et al. |
| 6,630,054 B1 | 10/2003 | Graef et al. |
| 6,649,025 B2 | 11/2003 | Mills et al. |
| 6,657,101 B1 | 12/2003 | Malmgren et al. |
| 6,663,611 B2 | 12/2003 | Blaney et al. |
| 6,670,522 B1 | 12/2003 | Graef et al. |
| 6,673,980 B1 | 1/2004 | Varona et al. |
| 6,673,983 B1 | 1/2004 | Graef et al. |
| 6,682,215 B2 | 1/2004 | Kinsley, Jr. et al. |
| 6,689,934 B2 | 2/2004 | Dodge, II et al. |
| 6,692,603 B1 | 2/2004 | Lindsay et al. |
| 6,703,330 B1 | 3/2004 | Marsh |
| 6,706,944 B2 | 3/2004 | Qin et al. |
| 6,709,548 B2 | 3/2004 | Marinack et al. |
| 6,709,550 B2 | 3/2004 | Holz et al. |
| 6,733,631 B2 | 5/2004 | Elonen et al. |
| 6,734,335 B1 | 5/2004 | Graef et al. |
| 6,746,570 B2 | 6/2004 | Burazin et al. |
| 6,749,719 B2 | 6/2004 | Burazin et al. |
| 6,750,262 B1 | 6/2004 | Hähnle et al. |
| 6,752,907 B2 | 6/2004 | Edwards et al. |
| 6,780,356 B1 | 8/2004 | Putt et al. |
| 6,787,000 B2 | 9/2004 | Burazin et al. |
| 6,790,314 B2 | 9/2004 | Burazin et al. |
| 6,797,114 B2 | 9/2004 | Hu |
| 6,808,790 B2 | 10/2004 | Chen et al. |
| 6,821,385 B2 | 11/2004 | Burazin et al. |
| 6,821,387 B2 | 11/2004 | Hu |
| 6,821,388 B2 | 11/2004 | Marsh |
| 6,824,650 B2 | 11/2004 | Lindsay et al. |
| 6,830,656 B2 | 12/2004 | Kinsley, Jr. |
| 6,837,956 B2 | 1/2005 | Cowell et al. |
| 6,837,972 B2 | 1/2005 | Marsh |
| 6,861,477 B2 | 3/2005 | Wang et al. |
| 6,867,346 B1 | 3/2005 | Dopps et al. |
| 6,875,315 B2 | 4/2005 | Bakken et al. |
| 6,878,238 B2 | 4/2005 | Bakken et al. |
| 6,887,348 B2 | 5/2005 | Hermans et al. |
| 6,893,535 B2 | 5/2005 | Hermans et al. |
| 6,921,459 B2 | 7/2005 | Kinsley, Jr. et al. |
| 6,939,914 B2 | 9/2005 | Qin et al. |
| 6,946,058 B2 | 9/2005 | Hu |
| 6,951,598 B2 | 10/2005 | Flugge et al. |
| 6,956,009 B2 | 10/2005 | Wang et al. |
| 6,962,645 B2 | 11/2005 | Graef et al. |
| 6,964,725 B2 | 11/2005 | Shannon et al. |
| 6,964,726 B2 | 11/2005 | Chen et al. |
| 6,969,781 B2 | 11/2005 | Graef et al. |
| 6,983,821 B2 | 1/2006 | Putt et al. |
| D517,816 S | 3/2006 | Dwiggins et al. |
| D519,739 S | 5/2006 | Schuh et al. |
| 7,041,196 B2 | 5/2006 | Lorenz et al. |
| 7,045,026 B2 | 5/2006 | Lorenz et al. |
| 7,052,580 B2 | 5/2006 | Trokhan et al. |
| 7,066,006 B2 | 6/2006 | Minerath, III et al. |
| 7,067,038 B2 | 6/2006 | Trokhan et al. |
| 7,081,559 B2 | 7/2006 | Fujikawa et al. |
| 7,125,470 B2 | 10/2006 | Graef et al. |
| 7,141,142 B2 | 11/2006 | Burazin et al. |
| 7,155,991 B2 | 1/2007 | Minerath, III et al. |
| 7,156,954 B2 | 1/2007 | Farrington, Jr. et al. |
| 7,160,418 B2 | 1/2007 | Edwards et al. |
| 7,166,190 B2 | 1/2007 | Graef et al. |
| 7,169,451 B2 | 1/2007 | Clarke et al. |
| 7,182,837 B2 | 2/2007 | Chen et al. |
| 7,214,293 B2 | 5/2007 | Trokhan et al. |
| 7,220,821 B2 | 5/2007 | Hähnle et al. |
| 7,229,528 B2 | 6/2007 | Vinson et al. |
| 7,235,708 B2 | 6/2007 | Guidotti et al. |
| D551,406 S | 9/2007 | Caruso et al. |
| 7,285,183 B2 | 10/2007 | Kajander et al. |
| 7,287,650 B2 | 10/2007 | Koslow |
| 7,291,382 B2 | 11/2007 | Krueger et al. |
| 7,294,238 B2 | 11/2007 | Bakken et al. |
| 7,300,547 B2 | 11/2007 | Luu et al. |
| 7,311,800 B2 | 12/2007 | Russell et al. |
| 7,314,663 B2 | 1/2008 | Stelljes, Jr. et al. |
| 7,314,664 B2 | 1/2008 | Stelljes, Jr. et al. |
| 7,314,665 B2 | 1/2008 | Stelljes, Jr. et al. |
| 7,322,970 B2 | 1/2008 | Schmidt et al. |
| 7,354,502 B2 | 4/2008 | Polat et al. |
| 7,364,015 B2 | 4/2008 | Englert et al. |
| 7,374,638 B2 | 5/2008 | Horenziak et al. |
| 7,390,378 B2 | 6/2008 | Carels et al. |
| 7,396,436 B2 | 7/2008 | Trokhan et al. |
| 7,407,560 B2 | 8/2008 | Hilbig et al. |
| 7,413,629 B2 | 8/2008 | Fisher et al. |
| 7,416,637 B2 | 8/2008 | Murray et al. |
| 7,435,266 B2 | 10/2008 | Sun et al. |
| 7,435,313 B2 | 10/2008 | Boatman et al. |
| 7,435,316 B2 | 10/2008 | Boatman et al. |
| 7,494,563 B2 | 2/2009 | Edwards et al. |
| 7,497,923 B2 | 3/2009 | Ward et al. |
| 7,497,925 B2 | 3/2009 | Hermans et al. |
| 7,497,926 B2 | 3/2009 | Hermans et al. |
| 7,503,998 B2 | 3/2009 | Murray et al. |
| 7,524,399 B2 | 4/2009 | Hermans et al. |
| 7,524,404 B2 | 4/2009 | Boatman et al. |
| 7,585,388 B2 | 9/2009 | Yeh et al. |
| 7,585,389 B2 | 9/2009 | Yeh et al. |
| 7,597,777 B2 | 10/2009 | Wilke, II |
| 7,601,374 B2 | 10/2009 | Clarke |
| 7,629,043 B2 | 12/2009 | Lindsay et al. |
| 7,645,359 B2 | 1/2010 | Lorenz et al. |
| 7,662,257 B2 | 2/2010 | Edwards et al. |
| 7,670,457 B2 | 3/2010 | Murray et al. |
| 7,678,229 B2 | 3/2010 | Wilke, II |
| 7,678,442 B2 | 3/2010 | Casey et al. |
| 7,682,697 B2 | 3/2010 | Raghavendran et al. |
| 7,691,228 B2 | 4/2010 | Edwards et al. |
| 7,699,959 B2 | 4/2010 | Ward et al. |
| 7,744,576 B2 | 6/2010 | Busam et al. |
| 7,750,203 B2 | 7/2010 | Becker et al. |
| 7,775,958 B2 | 8/2010 | Mukai et al. |
| 7,785,696 B2 | 8/2010 | Boatman et al. |
| 7,794,565 B2 | 9/2010 | Shannon et al. |
| 7,799,161 B2 | 9/2010 | Schuh et al. |
| 7,799,968 B2 | 9/2010 | Chen et al. |
| 7,820,008 B2 | 10/2010 | Edwards et al. |
| 7,828,932 B2 | 11/2010 | Hermans et al. |

(56) References Cited

U.S. PATENT DOCUMENTS

| | | |
|---|---|---|
| 7,846,296 B2 | 12/2010 | Luu et al. |
| 7,850,823 B2 | 12/2010 | Chou et al. |
| 7,851,057 B2 | 12/2010 | Englert et al. |
| 7,851,667 B2 | 12/2010 | Becker et al. |
| 7,857,941 B2 | 12/2010 | Ruthven et al. |
| 7,862,686 B2 | 1/2011 | Ward et al. |
| 7,887,676 B2 | 2/2011 | Boatman et al. |
| 7,918,951 B2 | 4/2011 | Lorenz et al. |
| 7,918,964 B2 | 4/2011 | Edwards et al. |
| 7,918,972 B2 | 4/2011 | Boatman et al. |
| 7,927,456 B2 | 4/2011 | Murray et al. |
| 7,972,476 B2 | 7/2011 | Scherb et al. |
| 7,994,079 B2 | 8/2011 | Chen et al. |
| 8,007,640 B2 | 8/2011 | Boatman et al. |
| 8,017,827 B2 | 9/2011 | Hundorf et al. |
| 8,056,733 B2 | 11/2011 | Koslow |
| 8,083,893 B2 | 12/2011 | Boatman et al. |
| 8,092,848 B2 | 1/2012 | Clarke |
| 8,102,275 B2 | 1/2012 | McGuire et al. |
| 8,110,232 B2 | 2/2012 | Clarke |
| 8,123,905 B2 | 2/2012 | Luu et al. |
| 8,142,612 B2 | 3/2012 | Murray et al. |
| 8,142,617 B2 | 3/2012 | Ruthven et al. |
| 8,143,472 B1 | 3/2012 | Bragd et al. |
| 8,152,957 B2 | 4/2012 | Edwards et al. |
| 8,152,958 B2 | 4/2012 | Super et al. |
| 8,158,689 B2 | 4/2012 | Baker et al. |
| 8,178,025 B2 | 5/2012 | Awofeso et al. |
| 8,187,240 B2 | 5/2012 | Busam et al. |
| 8,187,427 B2 | 5/2012 | Schuh et al. |
| 8,211,078 B2 | 7/2012 | Noel |
| 8,226,797 B2 | 7/2012 | Murray et al. |
| 8,257,552 B2 | 9/2012 | Edwards et al. |
| 8,293,072 B2 | 10/2012 | Super et al. |
| 8,319,005 B2 | 11/2012 | Becker et al. |
| 8,324,446 B2 | 12/2012 | Wang et al. |
| 8,328,985 B2 | 12/2012 | Edwards et al. |
| 8,361,278 B2 | 1/2013 | Fike et al. |
| 8,378,000 B2 | 2/2013 | Hintz et al. |
| 8,388,803 B2 | 3/2013 | Super et al. |
| 8,388,804 B2 | 3/2013 | Super et al. |
| 8,394,236 B2 | 3/2013 | Edwards et al. |
| 8,398,818 B2 | 3/2013 | Edwards et al. |
| 8,398,820 B2 | 3/2013 | Edwards et al. |
| 8,425,721 B2 | 4/2013 | Tynkkynen et al. |
| 8,435,381 B2 | 5/2013 | Murray et al. |
| 8,461,412 B2 | 6/2013 | Febo et al. |
| 8,496,637 B2 | 7/2013 | Hundorf et al. |
| 8,512,516 B2 | 8/2013 | Murray et al. |
| 8,524,040 B2 | 9/2013 | Edwards et al. |
| 8,540,846 B2 | 9/2013 | Miller et al. |
| 8,545,676 B2 | 10/2013 | Super et al. |
| 8,552,252 B2 | 10/2013 | Hundorf et al. |
| 8,562,786 B2 | 10/2013 | Murray et al. |
| 8,568,559 B2 | 10/2013 | Murray et al. |
| 8,568,560 B2 | 10/2013 | Murray et al. |
| 8,603,296 B2 | 12/2013 | Edwards et al. |
| 8,632,658 B2 | 1/2014 | Miller et al. |
| 8,636,874 B2 | 1/2014 | Super et al. |
| 8,647,105 B2 | 2/2014 | Awofeso et al. |
| 8,652,300 B2 | 2/2014 | Super et al. |
| 8,662,344 B2 | 3/2014 | Gispert |
| 8,673,115 B2 | 3/2014 | Edwards et al. |
| 8,674,170 B2 | 3/2014 | Busam et al. |
| 8,702,668 B2 | 4/2014 | Noel |
| 8,741,105 B2 | 6/2014 | Beaupre et al. |
| 8,741,427 B2 | 6/2014 | Kim et al. |
| 8,766,031 B2 | 7/2014 | Becker et al. |
| 8,778,138 B2 | 7/2014 | Super et al. |
| 8,791,318 B2 | 7/2014 | Becker et al. |
| 8,815,056 B2 | 8/2014 | Araki et al. |
| 8,829,263 B2 | 9/2014 | Haggstrom et al. |
| 8,841,506 B2 | 9/2014 | Febo et al. |
| 8,852,397 B2 | 10/2014 | Super et al. |
| 8,864,944 B2 | 10/2014 | Miller et al. |
| 8,864,945 B2 | 10/2014 | Miller et al. |
| 8,911,592 B2 | 12/2014 | Edwards et al. |
| 8,968,516 B2 | 3/2015 | Super et al. |
| 8,979,815 B2 | 3/2015 | Roe et al. |
| 8,980,052 B2 | 3/2015 | Super et al. |
| 9,017,517 B2 | 4/2015 | Super et al. |
| 9,044,359 B2 | 6/2015 | Wciorka et al. |
| 9,051,691 B2 | 6/2015 | Miller et al. |
| 9,057,158 B2 | 6/2015 | Miller et al. |
| 9,138,360 B1 | 9/2015 | Febo et al. |
| 9,144,524 B2 | 9/2015 | Febo et al. |
| 9,216,116 B2 | 12/2015 | Roe et al. |
| 9,216,118 B2 | 12/2015 | Roe et al. |
| 9,228,048 B2 | 1/2016 | Wibaux et al. |
| 9,241,845 B2 | 1/2016 | Hundorf et al. |
| 9,243,367 B2 | 1/2016 | Rekoske et al. |
| 9,267,240 B2 | 2/2016 | Lee et al. |
| 9,279,219 B2 | 3/2016 | Edwards et al. |
| 9,309,627 B2 | 4/2016 | Miller et al. |
| 9,326,896 B2 | 5/2016 | Schäfer et al. |
| 9,333,120 B2 | 5/2016 | Lavon et al. |
| 9,334,610 B2 | 5/2016 | Kinnunen et al. |
| 9,340,363 B2 | 5/2016 | Jackels et al. |
| 9,365,977 B2 | 6/2016 | Beaupre et al. |
| 9,371,614 B2 | 6/2016 | Schuh et al. |
| 9,371,615 B2 | 6/2016 | Super et al. |
| 9,375,358 B2 | 6/2016 | Ehrnsperger et al. |
| 9,382,665 B2 | 7/2016 | Miller et al. |
| 9,388,534 B2 | 7/2016 | Super et al. |
| 9,447,543 B2 | 9/2016 | Matula |
| 9,468,566 B2 | 10/2016 | Rosati et al. |
| 9,476,162 B2 | 10/2016 | Lee et al. |
| 9,492,328 B2 | 11/2016 | Jackels et al. |
| 9,493,911 B2 | 11/2016 | Miller et al. |
| 9,532,910 B2 | 1/2017 | Rosati et al. |
| 9,572,728 B2 | 2/2017 | Ashton et al. |
| 9,579,238 B2 | 2/2017 | Noel |
| 9,603,755 B2 | 3/2017 | Tanaka |
| 9,649,232 B2 | 5/2017 | Hippe et al. |
| 9,649,830 B2 | 5/2017 | Rasch |
| 9,657,443 B2 | 5/2017 | Rekoske et al. |
| 9,662,246 B2 | 5/2017 | Collinson et al. |
| 9,668,926 B2 | 6/2017 | Jackels et al. |
| 9,708,774 B2 | 7/2017 | Lee et al. |
| 9,713,556 B2 | 7/2017 | Arizti et al. |
| 9,713,557 B2 | 7/2017 | Arizti et al. |
| 9,739,015 B2 | 8/2017 | Miller et al. |
| 9,744,755 B2 | 8/2017 | Thompson, Jr. et al. |
| 9,752,280 B2 | 9/2017 | Matula |
| 9,763,835 B2 | 9/2017 | Becker et al. |
| 9,771,675 B2 | 9/2017 | Altshuler et al. |
| 9,789,009 B2 | 10/2017 | Joseph |
| 9,789,011 B2 | 10/2017 | Roe et al. |
| 9,808,554 B2 | 11/2017 | Swaniker |
| 9,822,487 B2 | 11/2017 | Ahoniemi et al. |
| 9,877,872 B2 | 1/2018 | Mumby et al. |
| 9,879,382 B2 | 1/2018 | Miller et al. |
| 9,950,309 B2 | 4/2018 | Lee et al. |
| 9,963,568 B2 | 5/2018 | Nakatsuji et al. |
| 9,974,697 B2 | 5/2018 | Lavon et al. |
| 9,974,699 B2 | 5/2018 | Kreuzer et al. |
| 9,987,176 B2 | 6/2018 | Roe et al. |
| 9,988,763 B2 | 6/2018 | Ramaratnam et al. |
| 9,994,712 B2 | 6/2018 | Cai et al. |
| 9,995,005 B2 | 6/2018 | Ramaratnam et al. |
| 10,004,647 B2 | 6/2018 | Jackels et al. |
| 10,022,280 B2 | 7/2018 | Ehrnsperger et al. |
| 10,034,800 B2 | 7/2018 | Febo et al. |
| 10,039,673 B2 | 8/2018 | Mumby et al. |
| 10,039,676 B2 | 8/2018 | LaVon |
| 10,052,242 B2 | 8/2018 | Bianchi et al. |
| 10,065,175 B2 | 9/2018 | Lee et al. |
| 10,071,002 B2 | 9/2018 | Bianchi et al. |
| 10,076,449 B2 | 9/2018 | Allen et al. |
| 10,099,425 B2 | 10/2018 | Miller, IV et al. |
| 10,130,519 B2 | 11/2018 | Mumby et al. |
| 10,130,525 B2 | 11/2018 | Rosati et al. |
| 10,130,527 B2 | 11/2018 | Peri et al. |
| 10,137,039 B2 | 11/2018 | Stelzig et al. |

(56) References Cited

U.S. PATENT DOCUMENTS

| | | | |
|---|---|---|---|
| 10,138,600 B2 | 11/2018 | Jannari et al. |
| 10,149,788 B2 | 12/2018 | Kreuzer et al. |
| 10,190,263 B2 | 1/2019 | Ramaratnam et al. |
| 10,196,780 B2 | 2/2019 | Lee et al. |
| 10,201,644 B2 | 2/2019 | Haggstrom et al. |
| 10,208,426 B2 | 2/2019 | Sealey et al. |
| 10,221,350 B2 | 3/2019 | Shalagina et al. |
| 10,231,874 B2 | 3/2019 | Mumby et al. |
| 10,245,188 B2 | 4/2019 | Jackels et al. |
| 10,247,195 B2 | 4/2019 | Manninen et al. |
| 10,259,151 B2 | 4/2019 | Kiiskinen et al. |
| 10,273,635 B2 | 4/2019 | Miller, IV et al. |
| 10,292,875 B2 | 5/2019 | Tapp et al. |
| 10,301,775 B2 | 5/2019 | Nordström et al. |
| 10,301,779 B2 | 5/2019 | Sealey, II et al. |
| 10,322,040 B2 | 6/2019 | Stiehl et al. |
| 10,335,324 B2 | 7/2019 | Roe et al. |
| 10,619,303 B2 | 4/2020 | Thole et al. |
| 11,015,292 B2 | 5/2021 | Venema et al. |
| 11,136,700 B2 | 10/2021 | Venema et al. |
| 11,313,061 B2 * | 4/2022 | Nhan .................. D04H 1/76 |
| 11,788,221 B2 * | 10/2023 | Nhan .................. D04H 1/5412 |
| | | 442/335 |
| 2001/0013389 A1 | 8/2001 | Fingal et al. |
| 2002/0007169 A1 | 1/2002 | Graef et al. |
| 2002/0013560 A1 | 1/2002 | Erspamer et al. |
| 2002/0055310 A1 | 5/2002 | Falk et al. |
| 2002/0088581 A1 | 7/2002 | Graef et al. |
| 2002/0092634 A1 | 7/2002 | Rokman et al. |
| 2002/0117768 A1 * | 8/2002 | Laine .................. D21F 11/002 |
| | | 264/45.8 |
| 2002/0132121 A1 | 9/2002 | Palacio et al. |
| 2003/0106656 A1 | 6/2003 | Johnson et al. |
| 2003/0139715 A1 | 7/2003 | Dodge et al. |
| 2003/0167045 A1 | 9/2003 | Graef et al. |
| 2003/0171727 A1 | 9/2003 | Graef et al. |
| 2003/0201082 A1 | 10/2003 | Kinsley |
| 2003/0220039 A1 | 11/2003 | Chen et al. |
| 2004/0045685 A1 | 3/2004 | Horner et al. |
| 2004/0063367 A1 | 4/2004 | Dodge et al. |
| 2004/0065420 A1 | 4/2004 | Graef et al. |
| 2004/0084162 A1 | 5/2004 | Shannon et al. |
| 2004/0084164 A1 | 5/2004 | Shannon et al. |
| 2004/0096642 A1 | 5/2004 | Maruyama et al. |
| 2004/0110017 A1 | 6/2004 | Lonsky et al. |
| 2004/0111817 A1 | 6/2004 | Chen et al. |
| 2004/0112783 A1 | 6/2004 | Mukai et al. |
| 2004/0115419 A1 | 6/2004 | Qin et al. |
| 2004/0115451 A1 | 6/2004 | Lonsky et al. |
| 2004/0121680 A1 | 6/2004 | Yahiaoui et al. |
| 2004/0127873 A1 | 7/2004 | Varona et al. |
| 2004/0142620 A1 | 7/2004 | Kinsley |
| 2004/0157524 A1 | 8/2004 | Polat et al. |
| 2004/0254551 A1 | 12/2004 | Carnes et al. |
| 2004/0256066 A1 | 12/2004 | Lindsay et al. |
| 2005/0034826 A1 | 2/2005 | Hu |
| 2005/0060933 A1 | 3/2005 | Henson |
| 2005/0090789 A1 | 4/2005 | Graef et al. |
| 2005/0095980 A1 | 5/2005 | Chang |
| 2005/0124709 A1 | 6/2005 | Krueger et al. |
| 2005/0136772 A1 | 6/2005 | Chen et al. |
| 2005/0142348 A1 | 6/2005 | Kajander et al. |
| 2005/0152954 A1 | 7/2005 | Farrell et al. |
| 2005/0230069 A1 | 10/2005 | Hilbig et al. |
| 2005/0244627 A1 | 11/2005 | Travelute et al. |
| 2005/0247397 A1 | 11/2005 | Kraus et al. |
| 2005/0247416 A1 | 11/2005 | Forry et al. |
| 2005/0267226 A1 | 12/2005 | Wehr et al. |
| 2006/0005916 A1 | 1/2006 | Stelljes et al. |
| 2006/0011315 A1 | 1/2006 | Kinsley et al. |
| 2006/0030632 A1 | 2/2006 | Krueger et al. |
| 2006/0063456 A1 | 3/2006 | Carter |
| 2006/0081348 A1 | 4/2006 | Graef et al. |
| 2006/0135026 A1 | 6/2006 | Arendt et al. |
| 2006/0142719 A1 | 6/2006 | Vogt et al. |
| 2006/0191357 A1 | 8/2006 | Minerath et al. |
| 2006/0266485 A1 | 11/2006 | Knox et al. |
| 2006/0266487 A1 | 11/2006 | Scherb et al. |
| 2007/0148433 A1 | 6/2007 | Mallory et al. |
| 2007/0179210 A1 | 8/2007 | Swaniker |
| 2007/0218485 A1 | 9/2007 | Davis et al. |
| 2007/0269644 A1 | 11/2007 | Harper et al. |
| 2008/0052859 A1 | 3/2008 | Orlandi |
| 2008/0179775 A1 | 7/2008 | Palm et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312625 A1 | 12/2008 | Hundorf et al. |
| 2008/0312628 A1 | 12/2008 | Hundorf et al. |
| 2009/0000753 A1 | 1/2009 | Vestola et al. |
| 2009/0001635 A1 | 1/2009 | Newson et al. |
| 2009/0008275 A1 | 1/2009 | Ferrari et al. |
| 2009/0117365 A1 | 5/2009 | Mallory et al. |
| 2009/0131898 A1 | 5/2009 | Malmgren et al. |
| 2009/0205794 A1 | 8/2009 | Scherb et al. |
| 2009/0270005 A1 | 10/2009 | Takahashi et al. |
| 2010/0006498 A1 | 1/2010 | Duello et al. |
| 2010/0075858 A1 | 3/2010 | Davis et al. |
| 2010/0132144 A1 | 6/2010 | Rautray |
| 2010/0136294 A1 | 6/2010 | Manifold et al. |
| 2010/0251611 A1 | 10/2010 | Henson |
| 2010/0273716 A1 | 10/2010 | Harris |
| 2010/0327484 A1 | 12/2010 | Schuh et al. |
| 2012/0121674 A1 | 5/2012 | Pedoja |
| 2012/0276337 A1 | 11/2012 | Curro et al. |
| 2013/0101805 A1 | 4/2013 | Altshuler et al. |
| 2013/0108831 A1 | 5/2013 | Wu et al. |
| 2014/0102650 A1 | 4/2014 | Qin et al. |
| 2014/0189970 A1 | 7/2014 | Fingal et al. |
| 2014/0231037 A1 | 8/2014 | Beaupre et al. |
| 2014/0324007 A1 | 10/2014 | Hundorf et al. |
| 2014/0366293 A1 | 12/2014 | Roe et al. |
| 2015/0038933 A1 | 2/2015 | Day et al. |
| 2015/0144829 A1 | 5/2015 | Grünbauer |
| 2015/0284911 A1 | 10/2015 | Juvonen et al. |
| 2016/0017112 A1 | 1/2016 | Naruse et al. |
| 2016/0219810 A1 | 8/2016 | Erkkilä et al. |
| 2016/0353820 A1 | 12/2016 | Baychar |
| 2017/0007079 A1 | 1/2017 | Janese |
| 2017/0258649 A1 | 9/2017 | Rosati et al. |
| 2017/0335521 A1 | 11/2017 | Lee |
| 2017/0335522 A1 | 11/2017 | Heiskanen et al. |
| 2017/0362775 A1 | 12/2017 | Juvonen et al. |
| 2018/0119353 A1 | 5/2018 | Tolfsson et al. |
| 2018/0327973 A1 | 11/2018 | Siitonen et al. |
| 2018/0355527 A1 | 12/2018 | Strandqvist et al. |
| 2019/0161915 A1 | 5/2019 | Swails et al. |
| 2021/0290450 A1 | 9/2021 | Nhan et al. |
| 2021/0292948 A1 | 9/2021 | Nhan et al. |
| 2024/0060222 A1 * | 2/2024 | Nhan .................. A61F 13/15577 |

FOREIGN PATENT DOCUMENTS

| | | |
|---|---|---|
| AT | 519423 A3 | 8/2018 |
| AU | 281485 B | 2/1965 |
| AU | 1973057198 A | 1/1975 |
| AU | 700394 B2 | 1/1999 |
| AU | 721197 B2 | 6/2000 |
| AU | 2002300959 | 6/2003 |
| AU | 2001285005 B2 | 2/2006 |
| AU | 2007272602 A1 | 1/2008 |
| AU | 2012298266 B2 | 6/2016 |
| BE | 436451 A | 9/1939 |
| CA | 949706 A | 6/1974 |
| CA | 979699 A | 12/1975 |
| CA | 2194176 A1 | 12/1996 |
| CA | 2868935 A1 | 9/2014 |
| CA | 2998561 A1 | 3/2018 |
| CN | 1173122 A | 2/1998 |
| CN | 1260977 A | 7/2000 |
| CN | 1270648 A | 10/2000 |

(56) References Cited

FOREIGN PATENT DOCUMENTS

| | | | | |
|---|---|---|---|---|
| CN | 1364182 A | 8/2002 | | |
| CN | 1094542 C | 11/2002 | | |
| CN | 1492954 A | * 4/2004 | ............. | B29C 44/20 |
| CN | 1518423 A | 8/2004 | | |
| CN | 103348062 A | 10/2013 | | |
| CN | 101410078 B | 2/2014 | | |
| CN | 103993498 B | 3/2016 | | |
| CN | 105828763 A | 8/2016 | | |
| CN | 105828764 A | 8/2016 | | |
| CN | 105899173 A | 8/2016 | | |
| CN | 104302834 B | 11/2016 | | |
| CN | 106456416 A | 2/2017 | | |
| CN | 107250458 A | 10/2017 | | |
| CN | 107460764 A | 12/2017 | | |
| CN | 107988838 A | 5/2018 | | |
| CN | 109937027 A | 6/2019 | | |
| DE | 2041406 A1 | 4/1971 | | |
| DE | 2263704 A1 | 8/1973 | | |
| DE | 2438587 A1 | 3/1975 | | |
| DE | 2902255 A1 | 7/1980 | | |
| DE | 3307736 A1 | 9/1984 | | |
| DE | 3420195 C2 | 6/1987 | | |
| DE | 4207233 A1 | 11/1993 | | |
| EP | 0101319 A3 | 3/1984 | | |
| EP | 0049944 B1 | 11/1984 | | |
| EP | 0136329 A4 | 1/1989 | | |
| EP | 0158938 B1 | 12/1989 | | |
| EP | 0296242 A4 | 7/1991 | | |
| EP | 0443082 A1 | 8/1991 | | |
| EP | 0242361 B1 | 9/1991 | | |
| EP | 0512819 A1 | 11/1992 | | |
| EP | 0150777 B2 | 11/1994 | | |
| EP | 0481745 B1 | 7/1996 | | |
| EP | 0537005 B1 | 7/1997 | | |
| EP | 0671504 B1 | 8/1997 | | |
| EP | 0696333 B1 | 3/1999 | | |
| EP | 0742858 B1 | 6/1999 | | |
| EP | 1160367 A2 | 12/2001 | | |
| EP | 1007784 B1 | 2/2003 | | |
| EP | 1145695 A3 | 1/2004 | | |
| EP | 1194644 B1 | 3/2004 | | |
| EP | 1400224 B1 | 3/2006 | | |
| EP | 1384457 B1 | 5/2006 | | |
| EP | 1808116 A1 | 7/2007 | | |
| EP | 1649094 B1 | 9/2007 | | |
| EP | 1442173 B1 | 3/2008 | | |
| EP | 1583865 B1 | 5/2008 | | |
| EP | 1463432 B1 | 8/2008 | | |
| EP | 1576233 B1 | 10/2008 | | |
| EP | 1813237 A3 | 12/2008 | | |
| EP | 1932968 B1 | 9/2009 | | |
| EP | 1967626 A4 | 9/2009 | | |
| EP | 1666240 B1 | 3/2011 | | |
| EP | 1440195 B1 | 8/2011 | | |
| EP | 1812637 B1 | 1/2012 | | |
| EP | 1950343 B1 | 4/2012 | | |
| EP | 1456472 B2 | 5/2012 | | |
| EP | 1497489 B1 | 8/2012 | | |
| EP | 1808152 B1 | 8/2012 | | |
| EP | 1567718 B1 | 4/2013 | | |
| EP | 2599915 A1 | 6/2013 | | |
| EP | 1268937 B1 | 2/2014 | | |
| EP | 2540892 B1 | 4/2014 | | |
| EP | 1876291 B1 | 9/2014 | | |
| EP | 2843130 A1 | 3/2015 | | |
| EP | 2952164 A1 | 12/2015 | | |
| EP | 2952165 A1 | 12/2015 | | |
| EP | 2737131 B1 | 1/2016 | | |
| EP | 1916333 B1 | 6/2016 | | |
| EP | 2001662 B1 | 6/2016 | | |
| EP | 1380401 B1 | 7/2016 | | |
| EP | 2807212 B1 | 4/2017 | | |
| EP | 2940210 B1 | 8/2017 | | |
| EP | 2622132 B1 | 4/2018 | | |
| EP | 3327395 A1 | 5/2018 | | |
| EP | 3162956 B1 | 3/2019 | | |
| EP | 3108060 B1 | 4/2021 | | |
| ES | 385106 A1 | 3/1973 | | |
| ES | 8606100 A1 | 4/1986 | | |
| ES | 2362723 T3 | 7/2011 | | |
| FI | 812601 A | 2/1982 | | |
| FI | 843904 A | 10/1984 | | |
| FI | 83741 C | 12/1992 | | |
| FI | 112812 B | 1/2004 | | |
| FI | 127377 B | 4/2018 | | |
| FI | 128917 B | 3/2021 | | |
| FR | 873763 A | 7/1942 | | |
| FR | 1449737 A | 8/1966 | | |
| FR | 1528992 A | 6/1968 | | |
| FR | 2206398 B3 | 9/1976 | | |
| GB | 598610 A | 2/1948 | | |
| GB | 1145484 A | 3/1969 | | |
| GB | 2109023 A | 5/1983 | | |
| GB | 2136813 A | 9/1984 | | |
| GB | 2116882 B | 10/1985 | | |
| GB | 2590316 A | * 6/2021 | ....... | A61F 13/15577 |
| IN | 1182DEL2005 A | 1/2007 | | |
| IN | 231170 B | 3/2009 | | |
| IN | 2957KOLNP2014 A | 5/2015 | | |
| IN | 3108MUM2014 A | 4/2016 | | |
| IN | 283291 B | 5/2017 | | |
| IN | 201717030330 A | 12/2017 | | |
| IN | 201837033267 A | 10/2018 | | |
| JP | 1983115199 A | 7/1983 | | |
| JP | 1989501859 A | 6/1989 | | |
| JP | 1993140886 A | 6/1993 | | |
| JP | 2002020999 A | 1/2002 | | |
| KR | 1020040088545 A | 10/2004 | | |
| KR | 100450272 B1 | 12/2005 | | |
| KR | 100637646 B1 | 10/2006 | | |
| KR | 100685522 B1 | 2/2007 | | |
| KR | 100725240 B1 | 6/2007 | | |
| KR | 1020100112299 A | 10/2010 | | |
| KR | 1020130077856 A | 7/2013 | | |
| KR | 101386319 B1 | 4/2014 | | |
| KR | 1020180007337 A | 1/2018 | | |
| RU | 2393093 C2 | 6/2010 | | |
| SE | 7304825 L | 11/1977 | | |
| SE | 7304888 L | 11/1977 | | |
| SE | 412881 B | 3/1980 | | |
| SE | 1651412 A1 | 4/2018 | | |
| SE | 540719 C2 | 10/2018 | | |
| WO | 1986003505 A1 | 6/1986 | | |
| WO | 1991010416 A1 | 7/1991 | | |
| WO | 1992003283 A1 | 3/1992 | | |
| WO | 1996031652 A1 | 10/1996 | | |
| WO | 9813181 A1 | 4/1998 | | |
| WO | 2000001882 A1 | 1/2000 | | |
| WO | 2000050694 A1 | 8/2000 | | |
| WO | 2001068793 A1 | 9/2001 | | |
| WO | 2001083866 A2 | 11/2001 | | |
| WO | 2002055788 A2 | 7/2002 | | |
| WO | 2003069038 A1 | 8/2003 | | |
| WO | 2004025009 A2 | 3/2004 | | |
| WO | 2004112956 A1 | 12/2004 | | |
| WO | 2005060712 A2 | 7/2005 | | |
| WO | 2006052967 A2 | 5/2006 | | |
| WO | 2006094077 A2 | 9/2006 | | |
| WO | 2007074625 A1 | 7/2007 | | |
| WO | 2009006371 A2 | 1/2009 | | |
| WO | 2009060118 A2 | 5/2009 | | |
| WO | 2011104427 A1 | 9/2011 | | |
| WO | 2012033449 A1 | 3/2012 | | |
| WO | 2014068196 A2 | 5/2014 | | |
| WO | 2014080084 A1 | 5/2014 | | |
| WO | 2014205048 A1 | 12/2014 | | |
| WO | 2015083092 A1 | 6/2015 | | |
| WO | 2015112155 A1 | 7/2015 | | |
| WO | 2015173474 A1 | 11/2015 | | |
| WO | 2016050901 A1 | 4/2016 | | |
| WO | 2016051350 A1 | 4/2016 | | |
| WO | 2016120528 A1 | 8/2016 | | |
| WO | 2016185398 A1 | 11/2016 | | |
| WO | 2016200299 A1 | 12/2016 | | |

(56) References Cited

FOREIGN PATENT DOCUMENTS

| WO | 2017006216 A1 | 1/2017 | | |
|----|---------------|--------|---|---|
| WO | 2017006241 A1 | 1/2017 | | |
| WO | 2017046751 A1 | 3/2017 | | |
| WO | 2017079169 A1 | 5/2017 | | |
| WO | 2017137879 A1 | 8/2017 | | |
| WO | 17156202 A1 | 9/2017 | | |
| WO | 2018002815 A1 | 1/2018 | | |
| WO | 2018011667 A1 | 1/2018 | | |
| WO | 2018041355 A1 | 3/2018 | | |
| WO | 2018065668 A1 | 4/2018 | | |
| WO | 2018116223 A1 | 6/2018 | | |
| WO | 2018152082 A1 | 8/2018 | | |
| WO | 2018171913 A1 | 9/2018 | | |
| WO | 2018171914 A1 | 9/2018 | | |
| WO | WO-2020023027 A1 * | 1/2020 | ....... | A61F 13/15577 |

* cited by examiner

PROCESS FOR MAKING THREE-DIMENSIONAL FOAM-LAID NONWOVENS

BACKGROUND

A bowel movement (BM) leaking from a diaper (i.e., leak around the leg area or at the waist) causes an unpleasant mess needing clean up by a caregiver. The consumer/chooser becomes dissatisfied with the absorbent product of choice, which can lead to the consumer/chooser deciding to switch to different diaper brand. As many as one in seven diapers containing BM result in BM leaking from the diaper. In addition, BM that is in contact with skin can result in compromising skin health and promoting development of diaper rash. Non-diaper skin can be healthier than diapered skin because current diapers do a poor job of keeping BM off of skin.

There is a lack of material/nonwoven solutions to reduce BM leakage occurrences and keep BM off of skin. Current materials in absorbent products, such as spunbond, SMS, and BCW, are mostly flat, dense, and do a poor job of handling runny BM and keeping BM off of skin. There are materials such as aperture films and textured BCW/SB composite nonwovens (e.g., TEXTOR brand nonwovens) that are used as liners. TEXTOR brand nonwovens can improve BM management properties compared to spunbond liner and is used in current products. Too many current products, however, that contain BM result in BM leakage. As a result, there is a great opportunity to identify materials that improve absorbent product BM management performance.

SUMMARY

The materials of the present disclosure are the next step in producing a diaper that completely absorbs runny BM at the point of insult, leaving no BM spreading and no BM on the skin, to deliver zero BM leakage and a cleaner skin experience. Identifying solutions to reduce BM blow outs and BM on skin is beneficial both to the wearer of the product and because it would result in a consumers having a more positive experience with such products by reducing the occurrence of diaper rash and providing a point of differentiation from other products.

The solutions disclosed herein are nonwoven materials having high degrees of three-dimensional (3D) topography and that have high compression resistance while also having a high level of openness. Such materials have demonstrated significantly better BM intake compared to current commercial materials being using in current products. The BM Flat Plate test method has demonstrated that three-dimensional foam-laid webs of the present disclosure reduce BM pooling to 2% wt/wt versus TEXTOR brand nonwovens at 40% wt/wt. BM pooling values are similar to rewet values and represent BM on skin.

The present disclosure describes novel extreme 3D nonwoven materials that have superior BM management properties. Such materials can improve absorbent products by reducing BM leakage and BM on skin. The nonwoven structures are made possible by templating foam-laid webs, otherwise labeled as 3D foam-laid nonwovens. The process involves dispersing bicomponent fibers in foam and templating such foam during drying & thermal bonding. This method results in extreme 3D nonwoven webs with features as high as 12 mm in height and as low as 8 mm in diameter. Because of these 3D features, there is high level of Z-direction fiber orientation that results in webs having high compression resistance while also having a high level of openness/porosity, which are key properties in being able to handle runny BM. In addition, a wide variety of 3D features, shapes, and sizes can be produced depending on template design.

The present disclosure is generally directed to a method for making a high topography nonwoven substrate, the method including generating a foam including water and synthetic binder fibers; depositing the foam on a planar surface; disposing a template form on the foam opposite the planar surface to create a foam/form assembly; heating the foam/form assembly to dry the foam and bind the synthetic binder fibers; and removing the template from the substrate after heating the foam/form assembly, wherein the substrate includes a planar base layer having an X-Y surface and a backside surface opposite the X-Y surface; and a plurality of projection elements integral with and protruding in a Z-direction from the X-Y surface, wherein each projection element has a height, a diameter or width, a cross-section, a sidewall, a proximal end where the projection element meets the base layer, and a distal end opposite the proximal end, wherein the projection elements are distributed in both the X- and Y-directions, and wherein the density of a projection element is the same as the density of the base layer.

In another aspect, the present disclosure is generally directed to a method for making a high topography nonwoven substrate, the method including generating a foam including water and synthetic binder fibers; depositing the foam on a planar surface; disposing a template form on the foam opposite the planar surface to create a foam/form assembly; heating the foam/form assembly to dry the foam and bind the synthetic binder fibers; and removing the template from the substrate after heating the foam/form assembly, wherein the substrate includes synthetic binder fibers, wherein the fibers of the substrate are entirely synthetic binder fibers; a planar base layer having an X-Y surface and a backside surface opposite the X-Y surface; and a plurality of projection elements integral with and protruding in a Z-direction from the X-Y surface, wherein each projection element has a height, a diameter or width, a cross-section, a sidewall, a proximal end where the projection element meets the base layer, and a distal end opposite the proximal end, wherein the projection elements are distributed in both the X- and Y-directions, wherein the shape of a cross-section of a projection element at the proximal end of the projection element is the same as the shape of a cross-section of a projection element at the distal end of the projection element, and wherein the density of a projection element is the same as the density of the base layer.

In still another aspect, the present disclosure is generally directed to a method for making a high topography nonwoven substrate, the method including generating a foam including water and synthetic binder fibers; depositing the foam on a planar surface; disposing a template form on the foam opposite the planar surface to create a foam/form assembly; heating the foam/form assembly to dry the foam and bind the synthetic binder fibers; and removing the template from the substrate after heating the foam/form assembly, wherein the substrate includes synthetic binder fibers, wherein the fibers of the substrate are entirely synthetic binder fibers, the substrate including a planar base layer having an X-Y surface and a backside surface opposite the X-Y surface; and a plurality of projection elements integral with and protruding in a Z-direction from the X-Y surface, wherein each projection element has a height, a diameter or width, a cross-section, a sidewall, a proximal end where the projection element meets the base layer, and a distal end opposite the proximal end, wherein the projection elements are distributed in both the X- and Y-directions, wherein each projection element has a uniform density, wherein the height of a projection element is greater than the width or diameter of that projection element, and wherein the density of a projection element is the same as the density of the base layer.

Various features and aspects of the present disclosure will be made apparent from the following detailed description.

BRIEF DESCRIPTION OF THE FIGURES

A full and enabling disclosure of the present disclosure, including the best mode thereof to one of ordinary skill in the art, is set forth more particularly in the specification, including reference to the accompanying figures in which.

Figure 1:
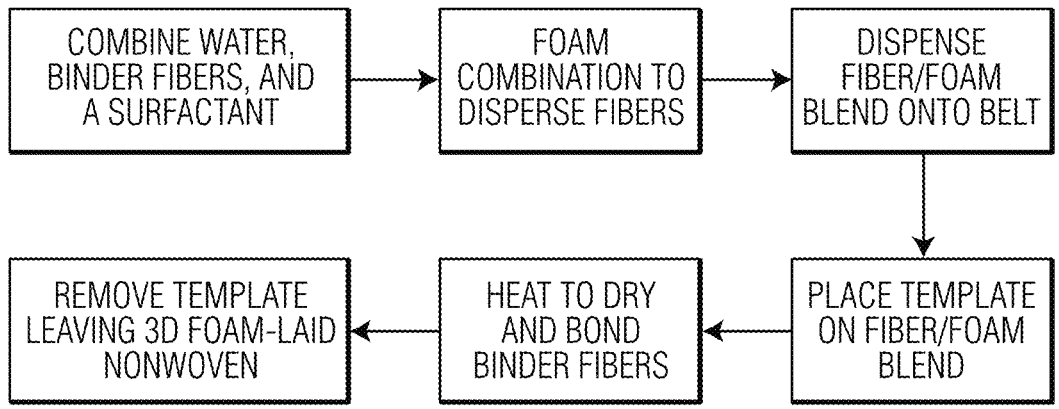
FIG. 1 is a flowchart view of an exemplary aspect of a process for producing 3D foam-laid nonwovens in accordance with the present disclosure.
Figure 2:
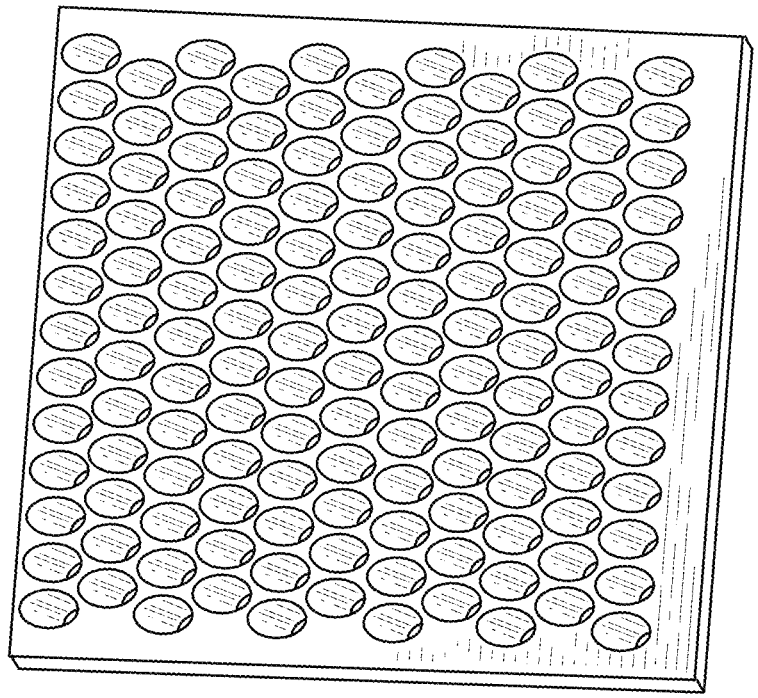
FIG. 2 is a perspective schematic illustration of one aspect of a template for use in the process of FIG. 1.

Repeated use of reference characters in the present specification and drawings is intended to represent the same or analogous features or elements of the present disclosure.

DETAILED DESCRIPTION

Reference now will be made to the aspects of the disclosure, one or more examples of which are set forth below. Each example is provided by way of explanation of the disclosure, not as a limitation of the disclosure. In fact, it will be apparent to those skilled in the art that various modifications and variations can be made in the disclosure without departing from the scope or spirit of the disclosure. For instance, features illustrated or described as part of one aspect can be used on another aspect to yield a still further aspect. Thus, it is intended that the present disclosure cover such modifications and variations as come within the scope of the appended claims and their equivalents. It is to be understood by one of ordinary skill in the art that the present discussion is a description of exemplary aspects only, and is not intended as limiting the broader aspects of the present disclosure, which broader aspects are embodied in the exemplary constructions.

The present disclosure describes novel extreme 3D nonwoven materials that have superior BM management properties. Such materials can improve absorbent products by reducing BM leakage and BM on skin. The nonwoven structures are made possible by templating foam-laid webs, otherwise labeled as 3D foam-laid webs. The process involves dispersing bicomponent fibers in foam and templating such foam during drying & thermal bonding. This method results in extreme 3D nonwoven webs with relatively tall and narrow 3D features. Because of these 3D features, there is high level of Z-direction fiber orientation that results in webs having high compression resistance while also having a high level of openness/porosity, which are key properties in being able to handle runny BM. In addition, a wide variety of 3D features, shapes, and sizes can be produced depending on template design.

Foam processes are normally used for making planar webs having a uniform thickness, such as two-dimensional shaped forms. As described herein, a three-dimensional nonwoven web is created by using a three-dimensional template to mold foam into a 3D topography. Drying and heating the templated foam results in a nonwoven having the topographical characteristics of the template.

The process of the present disclosure obviates any further molding of the nonwoven web as any desired topography is created along with the creation of the nonwoven. Prior methods of processing nonwovens require post-creation manipulation, cutting, embossing, or molding of an existing nonwoven web, resulting in weakening the web along with broad variations in web density and basis weight.

Creation of the nonwoven structures described herein requires three major steps: 1) Disperse binder fiber and a foaming agent in water to create a foam solution with a consistency some describe as shaving cream-like. 2) Template the fiber/foam blend. 3) Dry and heat the blend to remove water and to activate the binder fibers, thus setting the 3D structure in the nonwoven. These webs are referred to herein as 3D foam-laid nonwovens.

In the first step, binder fiber and a foaming agent are dispersed in water to create a foam solution with a consistency some describe as shaving cream-like. This step involves dispersing a blend of fibers capable of forming fiber-fiber bonds (e.g., bicomponent fibers/binder fibers) in a foam solution. This is done by mixing fibers, water, and foaming agent such as sodium dodecyl sulfate (SDS) surfactant simultaneously to create a foam and to uniformly suspend the fibers in the foam. This foaming process creates a stable foam containing a fibrous network that is uniformly dispersed through the foam solution. The foam has high viscosity, preventing fibers from floating, sinking, and/or agglomerating.

Many types of fibers can be included in the fiber blend, but the blend must include binder fibers in a quantity sufficient to ensure the final 3D foam-laid nonwoven has integrity and can maintain its 3D structural features. In one example, the fiber blend is 100% wt/wt binder fibers having a polyethylene sheath and a polypropylene core. The binder fibers are typically synthetic, thermoplastic bonder fibers. In other aspects, the binder fibers can be bi- and/or multi-component binder fibers. In other aspects, the fiber blend can include cellulosic fibers.

In another aspect of the present disclosure, nanovoided technology has produced lightweight, uncrimped bicomponent staple fiber with a fiber density reduction of 20-33%. Use of such lightweight fibers in the fiber blend can increase the fiber count for the same basis weight, thus increasing the web compression resistance. In various aspects, the low-density fiber can have density as low as 0.5 grams/cubic centimeter or even lower. In an example, the low density-voided fibers used can have a density of 0.62 g/cc, which equates to the polyolefin-based fiber having a 33% reduction in overall density with a 47% void volume in the core. Foam forming is a preferred method of forming a nonwoven web containing low-density fibers and enables lofty webs using voided fibers that do not require stuffer box crimped fibers. For example, carded webs require fibers to be stuffer box crimped to form a web. Stuff box crimping is a high pressure process that results in internal fiber void structure destruction and thus cannot generate a carded web including low-density voided fibers. Because of the high viscosity foam, low-density fibers are able to be properly laid into a web using the foam as carrier, thus enabling the ability to form webs including low-density fibers.

Although some level of binder fibers is required, the fiber blend does not need to contain solely binder fibers; other types of fibers can be incorporated into the fiber blend. The selection of fibers can include all types of synthetic fibers to a wide range of natural fibers. The fibers can have a wide range of cut length/fiber length, such as from 3-30 mm. A wide range of fiber diameters can also be used. A wide variety of foaming agents and amounts can be used such as anionic and non-ionic in amounts ranging from 0.1-5 wt %. Typically, SDS has been used at about 0.17 wt % to water. Foam density can range from 100-400 g/L. Foam stability half-life can range from 2-30 min. Fiber consistency (fiber concentration) can range from 0.5-5% wt/wt.

In the second step, the fiber/foam blend is poured onto or applied in any suitable manner to a foraminous belt or other suitable surface. The belt optionally includes a frame-type mold to limit the spread of the fiber/foam blend on the belt. A template is then placed on top of the fiber/foam blend, typically within the mold if present. The template provides a negative pattern to the desired pattern of the 3D foam-laid nonwoven. In one illustrative example, if a convex surface is desired for the nonwoven, then the template will have a concave surface pattern. Upon placement of the template, the fiber/foam blend conforms to the topography of the template, in essence creating bumps of foam where the template has dimples, dimples where the template has bumps, and flat spaces where the template is flat. In this manner, the template creates a 3D topography in the foam.

Typically the template contains cavities into which the fiber/foam blend can flow and fill. Cavity sizes range from 8 mm in diameter or larger and cavity depths can be as large as the thickness of the applied foam, as large as 50 mm or more. In one example, the template cavities are 12 mm deep. The cavities can have any suitable shape, including round, rectangular, square, triangular, mushroom-shaped, symbols, toroidal, or more complex combinations of shapes, and the template cavities can have any combination of shapes, sizes, and depths, or the template cavities can be of one uniform shape, size, and depth, as long as the fiber/foam blend can flow and fill the cavities in the template.

The template material should be selected to withstand bonding temperatures. Examples of template materials include silicon, metal, polyurethane, polytetrafluoroethylene, and any other suitable material. The template material should also be selected such that fibers do not adhere to template, thereby allowing easy removal of the web from the template, or the template from the web, after thermal activation of the binder fiber. In other words, the binder fibers should preferably adhere to other binder fibers rather than the template material. In general, increased fiber-to-fiber bonding overcomes fiber-to-template bonding problems. The template should also be open enough to allow proper air flow and heat transfer to enable drying and heat activation of the binder fiber.

In the third step, the templated fiber/foam blend is placed in an oven or other suitable heating device to dry and thermally bond the binder fibers. It is important that the template is present during the drying/bonding stage to ensure the 3D structure will be present in the final web. Temperatures and time in the oven should be long enough to remove a sufficient amount of water and to sufficiently activate the binding fiber. The time and temperature can be set by one skilled in the art based on the ingredients in the fiber/foam blend, the volume and surface area of the fiber/foam blend, the specifications of the oven used, the initial conditions of the templated fiber/foam blend, and any other relevant conditions.

The process described herein produces unique webs. Different high topography 3D nonwovens can be produced by selecting different templates (e.g., templates with different cavity sizes, shapes, depths, spacing, etc.). The 3D foam-laid nonwovens produced by the process described herein typically have a base layer defining an X-Y plane, where the base layer has an X-Y surface and a backside surface opposite the X-Y surface.

The 3D foam-laid nonwovens also include vertical (Z-direction) features such as projection elements protruding in the Z-direction from and integral with the base layer. This is often called a "peak and valley" type 3D structure. Each projection element has a height, a diameter or width, a cross-section, a sidewall, a proximal end where the projection element meets the base layer, and a distal end opposite the proximal end. The projection elements are typically distributed in both the X- and Y-directions. The projection elements can be uniformly distributed in both the X- and Y-directions, or the pattern of projection elements can be varied in either or both directions.

Depending on the template design, may different vertical feature shapes and sizes can be created. For example, a horizontal cross-section of a projection element can have any suitable shape, including round, rectangular, square, triangular, mushroom-shaped, symbols, toroidal, or more complex combinations of shapes. The height of the vertical features can range from 1 mm to 50 mm or greater, 1 mm to 30 mm, 5 mm to 50 mm, 5 mm to 30 mm, 30 mm to 50 mm, or any other suitable range of heights. The width or diameter of a vertical feature, depending on the shape of its cross-section, can be 8 mm or greater. The heights of the projection elements are preferably greater than the width or diameter of the projection elements. In various aspects, the ratio of the height of a projection element to the width or diameter of that projection element is greater than 0.5.

Because of the manner in which the 3D foam-laid nonwoven is produced, the density of a projection element is generally the same as or similar to the density of the base layer. In various aspects, the shape of a cross-section of a projection element at the proximal end of the projection element is the same as the shape of a cross-section of a projection element at the distal end of the projection element. Alternatively, the shape of a cross-section of a projection element at the proximal end of the projection element can be different from the shape of a cross-section of a projection element at the distal end of the projection element. The density of a projection element at the proximal end of the projection element can be the same as or different from the density of a projection element at the distal end of the projection element. The basis weight of a projection element at the proximal end of the projection element can be the same as or different from the density a projection element at the distal end of the projection element. In other aspects, the size of a cross-section of a projection element at the proximal end of the projection element can be the same as or different from the size of a cross-section of a projection element at the distal end of the projection element.

Each projection element can have an internally-uniform density. In other words, each projection element generally has a homogeneous density largely free of hollow or densified portions. The projection elements can have a density between 0.001 and 0.02 g/cc. The 3D foam-laid nonwovens demonstrate a basis weight range from 15 gsm to 120 gsm, although lower or higher basis weights can be produced using the process described herein.

Because of the manner in which the 3D foam-laid nonwoven is produced, the projection elements and particularly the sidewalls of the projection elements have fibers aligned in the Z-direction. In some aspects, the sidewalls have greater than 50 percent of fibers oriented in the Z-direction. Because of high degree of fiber z-direction orientation, the 3D foam-laid nonwovens described herein demonstrate very high compression resistance while also being very open and having a high level of porosity. For the purpose of comparison, "flat" bonded carded web (BCW) surge provides compression resistance of about 25 cc/g at 0.6 kPa pressure. The 3D foam-laid nonwovens of the present disclosure provide compression resistance from about 35 up to 65 cc/g at 0.6 kPa pressure. In addition, these high level of compression resistance is achievable with very open web structures. Again for the purpose of comparison, 100 gsm MGL9 surge, a standard BOW-type surge material, has an air permeability value of about 440 cfm, while the 3D foam-laid nonwovens measure between 1000 and 2500 cfm.

Bench testing of 3D foam-laid nonwovens has demonstrated superior BM management properties. For example, a test method for BM flow measures the amount of BM simulant that transfers from a BM-simulant-insulted nonwoven to blotter paper. A liner made from TEXTOR brand nonwoven typically results in about 40% of BM simulant remaining on the surface of the liner as shown using the blotter paper (i.e., the amount remaining is also called % pooled). The 3D foam-laid nonwovens of the present disclosure have demonstrated about half the amount of % pooling (i.e., 20%) compared to the TEXTOR brand nonwoven at about half the basis weight of TEXTOR brand nonwoven (55 gsm TEXTOR brand nonwoven compared to 30 gsm 3D foam-laid nonwoven). At higher basis weights, such as a 60 gsm 3D foam-laid nonwoven, demonstrated less than 2% BM simulant % pooled. The % pooled indicator can be consider analogous to "what is on skin" or rewet.

EXAMPLES

Procedures
Air Permeability Test

Air Permeability was measured in cubic feet of air per minute passing through a 38 square cm area (circle with 7 cm diameter) using a Textest FX3300 air permeability tester manufactured by Textest Ltd., Zurich, Switzerland. All tests were conducted in a laboratory with a temperature of 23±2° C. and 50±5% relative humidity. Specifically, a nonwoven sheet is allowed to dry out and condition for at least 12 hours in the 23±2° C. and 50±5% relative humidity laboratory before testing. The nonwoven sheet is clamped in the 7 cm diameter sheet test opening and the tester is set to a pressure drop of 125 Pa. Placing folds or crimps above the fabric test opening is to be avoided if at all possible. The unit is turned on by applying clamping pressure to the sample. The air flow under the 125 Pa pressure drop is recorded after 15 seconds of airflow to achieve a steady state value.

The Air Permeability Test measures the rate of airflow through a known dry specimen area. The air permeability of each sample was measured using a Textest FX3300 air permeability tester available from Schmid Corporation, having offices in Spartanburg, S. C.

A specimen from each test sample was cut and placed so the specimen extended beyond the clamping area of the air permeability tester. The test specimens were obtained from areas of the sample that were free of folds, crimp lines, perforations, wrinkles, and/or any distortions that make them abnormal from the rest of the test material.

The tests were conducted in a standard laboratory atmosphere of 23±1° C. (73.4±1.8° F.) and 50±2% relative humidity. The instrument was turned on and allowed to warm up for at least 5 minutes before testing any specimens. The instrument was calibrated based on the manufacturer's guidelines before the test material was analyzed. The pressure sensors of the instrument were reset to zero by pressing the NULL RESET button on the instrument. Before testing, and if necessary between samples or specimens, the dust filter screen was cleaned, following the manufacturer's instructions. The following specifications were selected for data collection: (a) Unit of measure: cubic feet per minute (cfm); (b) test pressure: 125 Pascal (water column 0.5 inch or 12.7 mm); and (c) test head: 38 square centimeters (cm 2). Because test results obtained with different size test heads are not always comparable, samples to be compared should be tested with the same size test head.

The NULL RESET button was pressed prior to every series of tests, or when the red light on the instrument was displayed. The test head was open (no specimen in place) and the vacuum pump was at a complete stop before the NULL RESET button was pressed.

Each specimen was placed over the lower test head of the instrument. The test was started by manually pressing down on the clamping lever until the vacuum pump automatically started. The Range Indicator light on the instrument was stabilized in the green or yellow area using the RANGE knob. After the digital display was stabilized, the air permeability of the specimen was displayed, and the value was recorded. The test procedure was repeated for 10 specimens of each sample, and the average value for each sample was recorded as the air permeability.

Compression Test Method

From the target nonwoven, a 38 mm by 25 mm test sample was cut. The upper and lower platens made of stainless steel were attached to a tensile tester (Model: Alliance RT/1 manufactured by MTS System Corporation, a business having a location in Eden Prairie, Minn., U.S.A.). The top platen had a diameter of 57 mm while the lower platen had a diameter of 89 mm. The upper platen was connected to a 100 N load cell while the lower platen was attached to the base of the tensile tester. TestWorks Version 4 software program provided by MTS was used to control the movement of the upper platen and record the load and the distance between the two platens. The upper platen was activated to slowly move downward and touch the lower platen until the compression load reached around 5000 g. At this point, the distance between the two platens was zero. The upper platen was then set to move upward (away from the lower platen) until the distance between the two platens reaches 15 mm. The crosshead reading shown on TestWorks Version 4 software program was set to zero. A test sample was placed on the center of the lower platen with the projections facing toward the upper platen. The upper platen was activated to descend toward the lower platen and compress the test sample at a speed of 25 mm/min. The distance that the upper platen travels was indicated by the crosshead reading. This was a loading process. When 345 grams of force (about 3.5 kPa) was reached, the upper platen stopped moving downward and returned at a speed of 25 mm/min to its initial position where the distance between the two platens was 15 mm. This was an unloading process. The compression load and the corresponding distance between the two platens during the loading and unloading were recorded on a computer using TestWorks Version 4 software program provided by MTS. The compression load was converted to the compression stress by dividing the compression force by the area of the test sample. The distance between the two platens at a given compression stress represented the thickness under that particular compression stress. A total of three test samples were tested for each test sample code to get representative loading and unloading curves for each test sample code.

Flow Through Test Method

The Flow Through Test was performed using Simulant A, which was applied to the targeted nonwoven. The BM simulant was applied using a BM gun and the absorption test conducted using the BM Plate Test Method. The targeted nonwoven was the material described herein. The four corners of the BM plate were then adjusted to match nonwoven thickness and checked to make sure the plate was level. The nonwoven was placed between the lower and upper plates and insulted with BM simulant. The nonwoven was left in the test apparatus for 2 minutes after insult, and then placed on a vacuum box to measure the amount of BM simulant pooling on the nonwoven. Four paper towels were placed on top of the nonwoven and the nonwoven was flipped with the paper towels down on top of the vacuum box and covered with a silicone sheet to seal the vacuum. The vacuum box was turned on pulling a pressure of 5 inches of water for 1 minute. In addition to the BM simulant picked-up by paper towels on the vacuum box, the excess BM simulant left on the BM plate was removed using an additional paper towel. The BM simulant amount picked up by the paper towels from the vacuum box along with the excess BM simulant left on the plate was recorded as the total pooled BM simulant.

Three (N=3) samples were tested for each of the examples. The amounts of BM simulant in each layer in the 3 samples were then averaged to get BM simulant pooled on the nonwoven.

Materials

Fibers

Voided bicomponent fibers with a diameter of 33 microns, a denier of 5.5 dpf, and a density of 0.705 g/cc. Non-voided bicomponent fibers with a diameter of 33 microns, a denier of 7.1 dpf, and a density of 0.913 g/cc. Note that the density of the voided bicomponent fibers was 23 percent less than the density of the non-voided bicomponent fibers. The fiber density was measured using sink/float after web thermal bonding at 133° C. The fibers were cut to a length of 18 mm, then heat set at 118° C. for a final length of 15 mm. The codes tested are listed in Table 1.

TABLE 1

Codes Tested

| Code Number | Fiber | Target Basis Weight, in gsm |
|---|---|---|
| 1 | Voided | 30 |
| 2 | Voided | 60 |
| 3 | Voided | 120 |
| 4 | Non-Voided | 30 |
| 5 | Non-Voided | 60 |
| 6 | Non-Voided | 120 |

The three-dimensional foam-laid handsheets tested herein were produced by combining 300 grams of deionized water, 5 grams of 10% SDS, and fibers. The combination was mixed to foam and poured into an 8 inch by 8 inch by 2 inch frame. This was then templated with a template having square holes of 1 cm, an openness of 40%, and a thickness of 12 mm, with a nylon spunbond backing. The assembly was dried and thermal bonded at 133° C. for 1 to 1.5 hours. This was then wet dipped in 0.2% wt/wt of SILWET brand DA63 surfactant in water and dried in ambient conditions.

Fecal Material Simulant

The following is a description of the fecal material simulant A used in the examples described herein.

Ingredients:
- DANNON brand All Natural Low-fat Yogurt (1.5% milk-fat grade A), Vanilla with other natural flavor, in 32 oz container.
- MCCORMICK brand Ground Turmeric
- GREAT VALUE brand 100% liquid egg whites
- KNOX brand Original Gelatin—unflavored and in powder form
- DAWN brand Ultra Concentrated original scent dishwashing liquid
- Distilled Water Note: All fecal material simulant ingredients can be purchased at grocery stores such as WAL-MART brand stores or through on-line retailers. Some of the fecal material simulant ingredients are perishable food items and should be incorporated into the fecal material simulant at least two weeks prior to their expiration date.

Mixing Equipment:
- Laboratory Scale with an accuracy to 0.01 gram
- 500 mL beaker
- Small lab spatula
- Stop watch
- IKA-WERKE brand Eurostar Power Control-Vise with R 1312 Turbine stirrer available from IKA Works, Inc., Wilmington, NC, USA.

Mixing Procedure:
1. A 4-part mixture is created at room temperature by adding, in the following order, the following fecal material simulant ingredients (which are at room temperature) to the beaker at a temperature between 21° C. and 25° C.: 57% yogurt, 3% turmeric, 39.6% egg white, and 0.4% gelatin. For example, for a total mixture weight of 200.0 g, the mixture will have 114.0 g of the yogurt, 6.0 g of the turmeric, 79.2 g of the egg whites, and 0.8 g of the gelatin.
2. The 4-part mixture should be stirred to homogeneity using the IKA-WERKE brand Eurostar stirrer set to a speed of 50 RPM. Homogeneity will be reached in approximately 5 minutes (as measured using the stop watch). The beaker position can be adjusted during stirring so the entire mixture is stirred uniformly. If any of the mixture material clings to the inside wall of the beaker, the small spatula is used to scrape the mixture material off the inside wall and place it into the center part of the beaker.
3. A 1.3% solution of DAWN brand dishwashing liquid is made by adding 1.3 grams of DAWN brand Ultra Concentrated dishwashing liquid into 98.7 grams of distilled water. The IKA-WERKE brand Eurostar and the R 1312 Turbine stirrer is used to mix the solution for 5 minutes at a speed of 50 RPM.
4. An amount of 2.0 grams of the 1.3% DAWN brand dishwashing liquid solution is added to 200 grams of the 4-part mixture obtained from Step 2 for a total combined weight of 202 grams of fecal material simulant. The 2.0 grams of the 1.3% DAWN brand dishwashing liquid solution is stirred into the homogenous 4-part mixture carefully and only to homogeneity (approximately 2 minutes) at a speed of 50 RPM, using the IKA-WERKE brand Eurostar stirrer. Final viscosity of the final fecal material simulant should be 390±40 cP (centipoise) when measured at a shear rate of 10 s$^{-1}$ and a temperature of 37° C.

5. The fecal material simulant is allowed to equilibrate for about 24 hours in a refrigerator at a temperature of 7° C. It can be stored in a lidded and airtight container and refrigerated for up to 5 days at around 7° C. Before use, the fecal material simulant should be brought to equilibrium with room temperature. It should be noted that multiple batches of fecal material simulant of similar viscosity can be combined. For example, five batches of fecal material simulant of similar viscosity and each 200 grams can be combined into one common container for a total volume of 1000 cc. It will take approximately 1 hour for 1000 cc of fecal material simulant to equilibrate with room temperature.

Results

Figure 3:
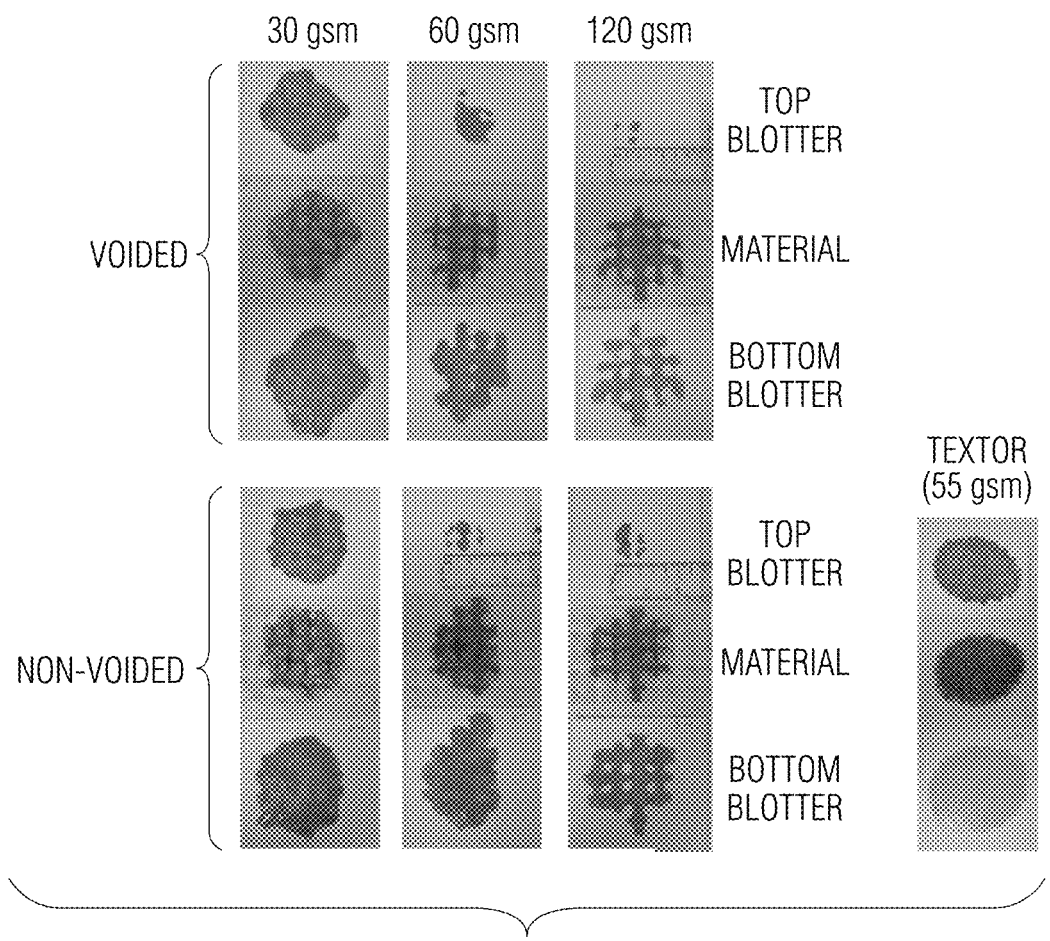
FIG. 3 photographically illustrates the results of Flow Through testing of various nonwovens including those produced by the process of FIG. 1.
Figure 4:
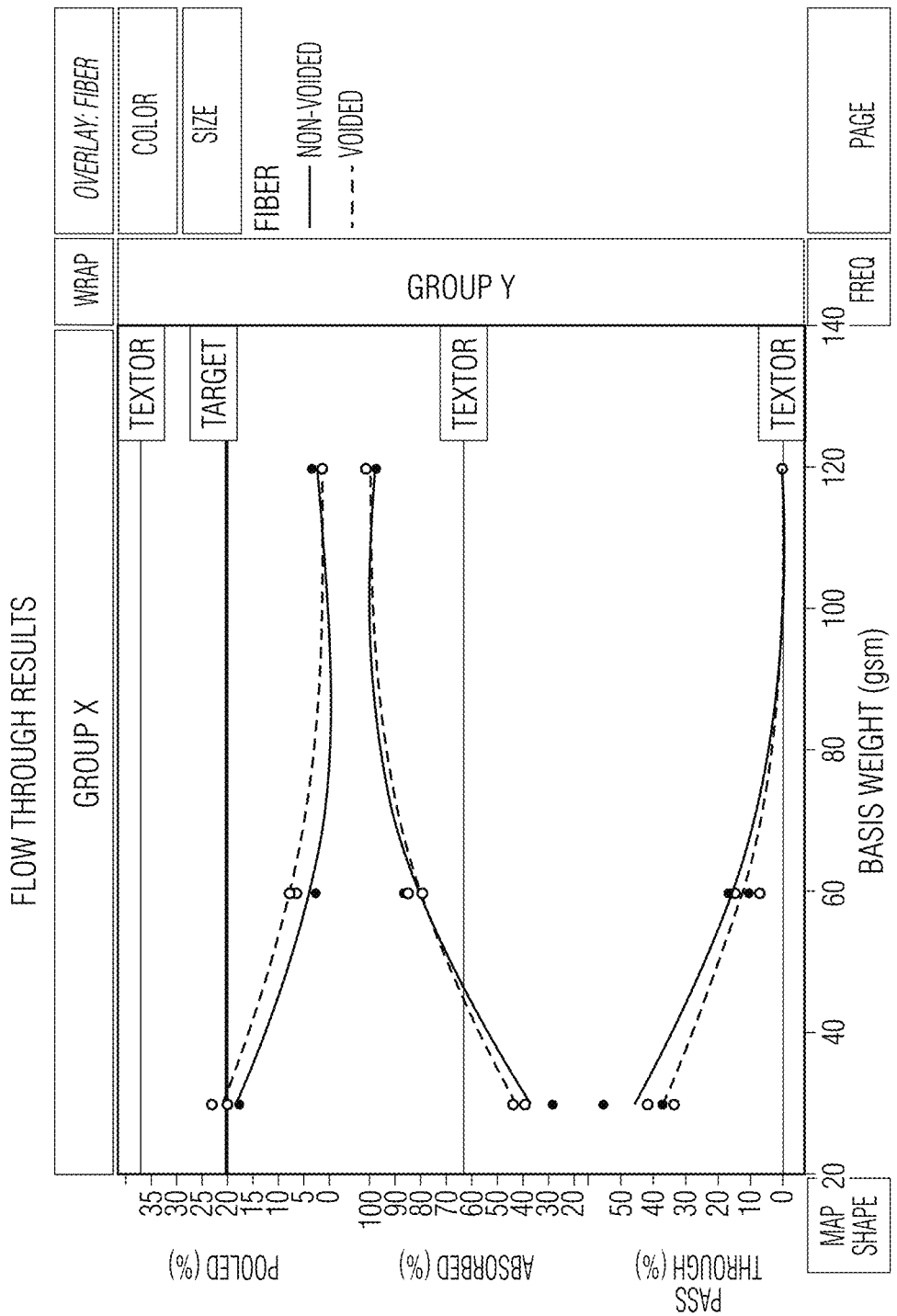
FIG. 4 graphically illustrates the results of Flow Through testing of various nonwovens including those produced by the process of FIG. 1.

Results of the Flow Through Tests are illustrated in FIGS. 3 and 4. 3D foam-laid nonwovens using voided and non-voided binder fibers behaved similarly in the tests. When compared to the results of the TEXTOR brand nonwoven test, the 3D foam-laid nonwoven test demonstrated approximately half the % pooling at nearly half the basis weight. Higher basis weight 3D foam-laid nonwovens demonstrated approximately less than 2% % pooling. In addition, there is a higher level of BM simulant passing through the 3D foam-laid nonwoven, even at a basis weight of 60 gsm.

Figure 5:
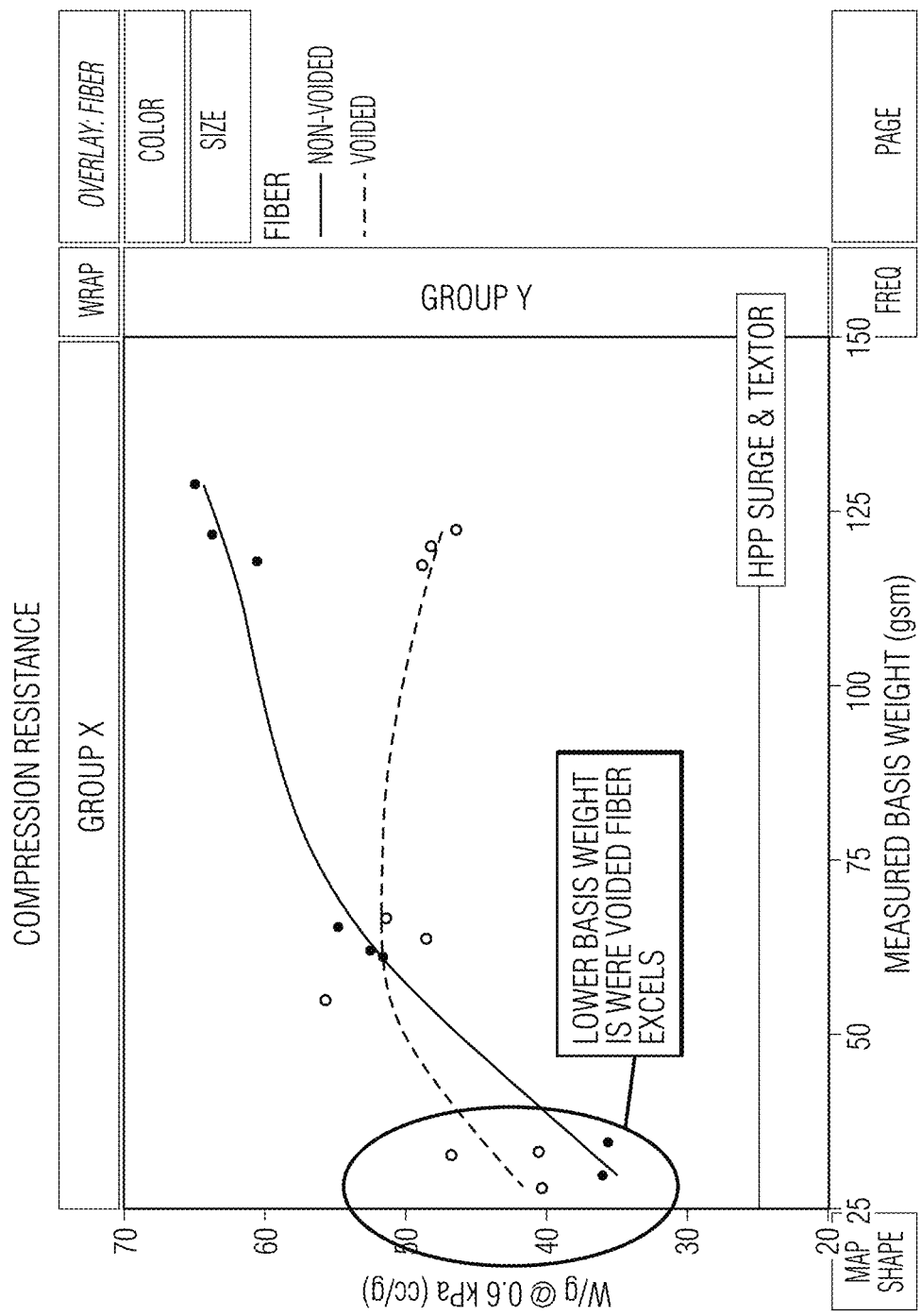
FIG. 5 graphically illustrates the results of Compression Resistance testing of various nonwovens including those produced by the process of FIG. 1.
Figure 6:
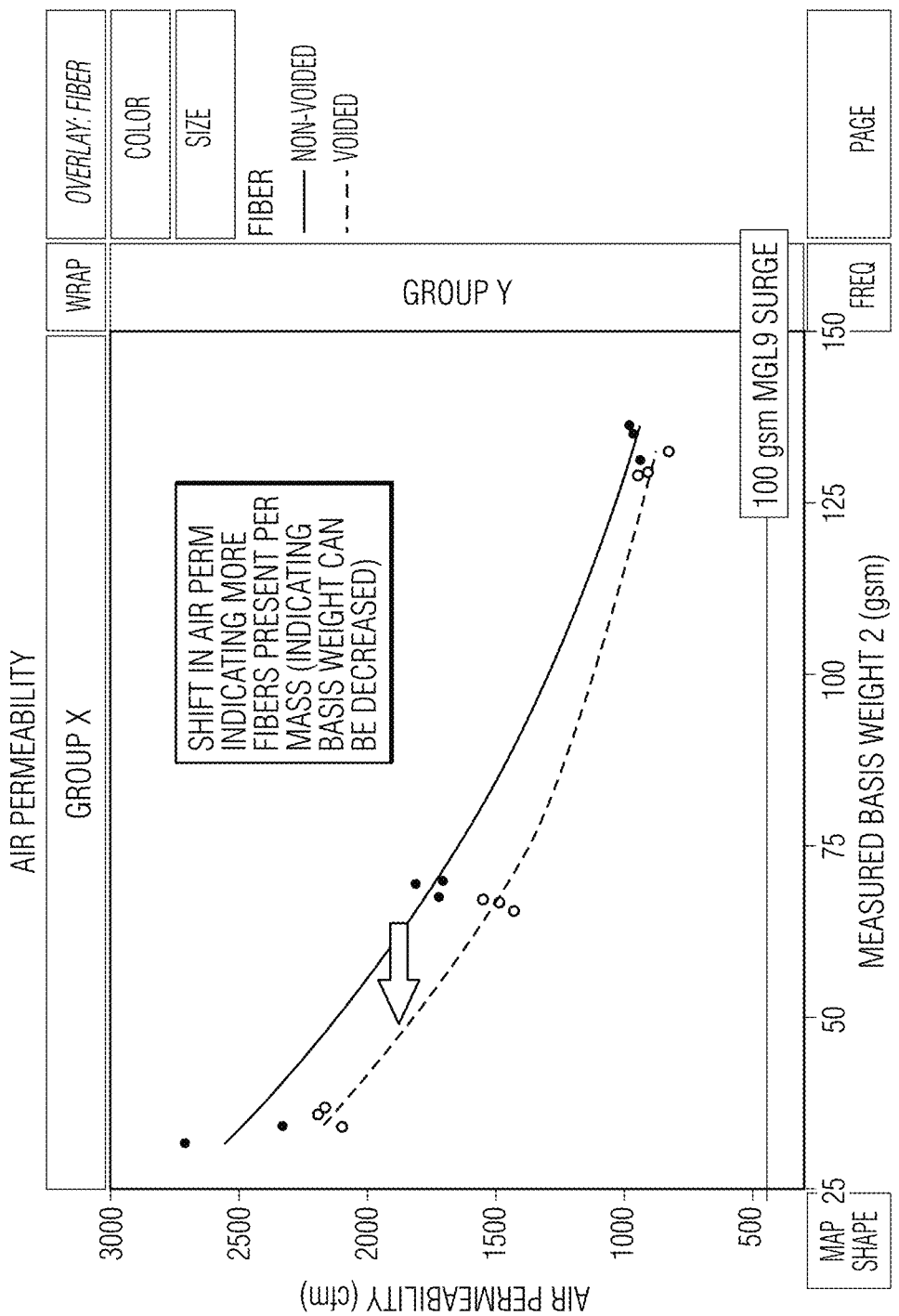
FIG. 6 graphically illustrates the results of Air Permeability testing of various nonwovens including those produced by the process of FIG. 1.

Results of compression and air permeability tests are illustrated in FIGS. 5 and 6. The 3D foam-laid nonwovens of the present disclosure exhibit high compression resistance and high air permeability. In this peak and valley model, the combination of open valleys and compression resistant peaks is an arrangement resulting in low % pooling values.

The solutions disclosed herein are nonwoven materials having high degrees of 3D topography, high compression resistance, and a high level of openness. Such materials demonstrate significantly better BM intake compared to current commercial materials used in current products. The BM Flat Plate test method has demonstrated that the 3D foam-laid nonwovens of the present disclosure can reduce BM pooling to 2% wt/wt, as compared to TEXTOR brand nonwovens at 40% wt/wt. BM pooling values can be considered analogous to rewet values and represent BM on skin.

In a first particular aspect, a method for making a high topography nonwoven substrate includes generating a foam including water and synthetic binder fibers; depositing the foam on a planar surface; disposing a template form on the foam opposite the planar surface to create a foam/form assembly; heating the foam/form assembly to dry the foam and bind the synthetic binder fibers; and removing the template from the substrate after heating the foam/form assembly, wherein the substrate includes a planar base layer having an X-Y surface and a backside surface opposite the X-Y surface; and a plurality of projection elements integral with and protruding in a Z-direction from the X-Y surface, wherein each projection element has a height, a diameter or width, a cross-section, a sidewall, a proximal end where the projection element meets the base layer, and a distal end opposite the proximal end, wherein the projection elements are distributed in both the X- and Y-directions, and wherein the density of a projection element is the same as the density of the base layer.

A second particular aspect includes the first particular aspect, wherein the binder fibers are bi- and/or multicomponent binder fibers.

A third particular aspect includes the first and/or second aspect, wherein the shape of a cross-section of a projection element at the proximal end of the projection element is the same as the shape of a cross-section of a projection element at the distal end of the projection element.

A fourth particular aspect includes one or more of aspects 1-3, wherein the shape of a cross-section of a projection element at the proximal end of the projection element is different from the shape of a cross-section of a projection element at the distal end of the projection element.

A fifth particular aspect includes one or more of aspects 1-4, wherein the shape of a cross-section of a projection element is circular, oval, rectangular, or square.

A sixth particular aspect includes one or more of aspects 1-5, wherein the density of a projection element at the proximal end of the projection element is the same as the density of a projection element at the distal end of the projection element.

A seventh particular aspect includes one or more of aspects 1-6, wherein the basis weight of a projection element at the proximal end of the projection element is the same as the density a projection element at the distal end of the projection element.

An eighth particular aspect includes one or more of aspects 1-7, wherein the size of a cross-section of a projection element at the proximal end of the projection element is different from the size of a cross-section of a projection element at the distal end of the projection element.

A ninth particular aspect includes one or more of aspects 1-8, wherein each projection element has a uniform density.

A tenth particular aspect includes one or more of aspects 1-9, wherein the height of a projection element is greater than the width or diameter of that projection element.

An eleventh particular aspect includes one or more of aspects 1-10, wherein the substrate has a compression resistance that provides 20 cubic centimeters or more of void volume per gram of substrate at 0.6 kPa pressure.

A twelfth particular aspect includes one or more of aspects 1-11, wherein the ratio of the height of a projection element to the width or diameter of a projection element is greater than 0.5.

A thirteenth particular aspect includes one or more of aspects 1-12, wherein the height of a projection element is greater than 3 mm.

A fourteenth particular aspect includes one or more of aspects 1-13, wherein the sidewalls have greater than 50 percent of fibers oriented in the Z-direction.

A fifteenth particular aspect includes one or more of aspects 1-14, wherein the synthetic binder fibers have an average length greater than 3 mm.

A sixteenth particular aspect includes one or more of aspects 1-15, wherein the projection elements have a density between 0.001 and 0.02 g/cc.

A seventeenth particular aspect includes one or more of aspects 1-16, wherein the projection elements are uniformly distributed in both the X- and Y-directions.

In an eighteenth particular aspect, a method for making a high topography nonwoven substrate includes generating a foam including water and synthetic binder fibers; depositing the foam on a planar surface; disposing a template form on the foam opposite the planar surface to create a foam/form assembly; heating the foam/form assembly to dry the foam and bind the synthetic binder fibers; and removing the template from the substrate after heating the foam/form assembly, wherein the substrate includes synthetic binder fibers, wherein the fibers of the substrate are entirely synthetic binder fibers; a planar base layer having an X-Y surface and a backside surface opposite the X-Y surface; and a plurality of projection elements integral with and protruding in a Z-direction from the X-Y surface, wherein each projection element has a height, a diameter or width, a cross-section, a sidewall, a proximal end where the projection element meets the base layer, and a distal end opposite the proximal end, wherein the projection elements are distributed in both the X- and Y-directions, wherein the shape of a cross-section of a projection element at the proximal end of the projection element is the same as the shape of a cross-section of a projection element at the distal end of the projection element, and wherein the density of a projection element is the same as the density of the base layer.

In a nineteenth particular aspect, a method for making a high topography nonwoven substrate includes generating a foam including water and synthetic binder fibers; depositing the foam on a planar surface; disposing a template form on the foam opposite the planar surface to create a foam/form assembly; heating the foam/form assembly to dry the foam and bind the synthetic binder fibers; and removing the template from the substrate after heating the foam/form assembly, wherein the substrate includes synthetic binder fibers, wherein the fibers of the substrate are entirely synthetic binder fibers, the substrate including a planar base layer having an X-Y surface and a backside surface opposite the X-Y surface; and a plurality of projection elements integral with and protruding in a Z-direction from the X-Y surface, wherein each projection element has a height, a diameter or width, a cross-section, a sidewall, a proximal end where the projection element meets the base layer, and a distal end opposite the proximal end, wherein the projection elements are distributed in both the X- and Y-directions, wherein each projection element has a uniform density, wherein the height of a projection element is greater than the width or diameter of that projection element, and wherein the density of a projection element is the same as the density of the base layer.

A twentieth particular aspect includes the nineteenth particular aspect, wherein the shape of a cross-section of a projection element at the proximal end of the projection element is the same as the shape of a cross-section of a projection element at the distal end of the projection element.

These and other modifications and variations to the present disclosure may be practiced by those of ordinary skill in the art, without departing from the spirit and scope of the present disclosure, which is more particularly set forth in the appended claims. In addition, it should be understood that aspects of the various aspects may be interchanged both in whole and in part. Furthermore, those of ordinary skill in the art will appreciate that the foregoing description is by way of example only, and is not intended to limit the disclosure so further described in such appended claims.

What is claimed:

1. A method for making a high topography nonwoven substrate, the method comprising:
   generating a foam including water, a foaming agent, and a plurality of fibers, the plurality of fibers comprising synthetic binder fibers;
   providing a template form;
   templating the foam to create a foam/form assembly;
   heating the foam to dry the foam and bind the synthetic binder fibers; and
   removing the template form after heating to provide the substrate, wherein the substrate includes a base layer having an X-Y surface and a backside surface opposite the X-Y surface, the base layer having a density; and
   a plurality of projection elements integral with and protruding in a Z-direction from the X-Y surface, wherein each projection element has a height, a diameter or width, a cross-section, a sidewall, a density, a proximal end where the projection element meets the base layer, and a distal end opposite the proximal end, and wherein the density of a projection element is the same as the density of the base layer.

2. The method of claim 1, wherein templating the foam to create the foam/form assembly comprises depositing the foam on a foraminous belt.

3. The method of claim 2, wherein the foraminous belt is planar.

4. The method of claim 2, wherein the foraminous belt includes a mold.

5. The method of claim 1, wherein the template form comprises cavities into which the foam can flow and fill and that provides a negative pattern to a desired pattern of the high topography nonwoven substrate.

6. The method of claim 1, wherein templating the foam to create the foam/form assembly comprises disposing the template form on the foam.

7. The method of claim 1, wherein the synthetic binder fibers are bi- and/or multi-component binder fibers.

8. The method of claim 1, wherein a shape of a cross-section of the projection element is circular, oval, rectangular, or square.

9. The method of claim 1, wherein a density of a projection element at the proximal end of the projection element is the same as a density of the projection element at the distal end of the projection element.

10. The method of claim 1, wherein a basis weight of a projection element at the proximal end of the projection element is the same as a basis weight of a projection element at the distal end of the projection element.

11. The method of claim 1, wherein each projection element has a uniform density.

12. A method for making a high topography nonwoven substrate, the method comprising:
   generating a foam including water, a foaming agent, and a plurality of fibers, the plurality of fibers comprising synthetic binder fibers;
   providing a template form comprising cavities into which the foam can flow and fill and that provides a negative pattern to a desired pattern of the high topography nonwoven substrate;
   templating the foam to create a foam/form assembly;
   heating the foam at a temperature and a length of time to remove water from the foam and bind at least some of the synthetic binder fibers; and
   removing the template form after heating to provide the substrate.

13. The method of claim 12, wherein templating the foam to create the foam/form assembly comprises depositing the foam on a foraminous belt.

14. The method of claim 13, wherein the foraminous belt is planar.

15. The method of claim 12, wherein templating the foam to create the foam/form assembly comprises disposing the template form on the foam.

16. The method of claim 12, wherein the synthetic binder fibers are bi- and/or multi-component binder fibers.

17. The method of claim 12, wherein a shape of a cross-section of the projection element is circular, oval, rectangular, or square.

18. The method of claim 12, wherein a density of a projection element at the proximal end of the projection element is the same as a density of the projection element at the distal end of the projection element.

19. The method of claim 12, wherein a basis weight of a projection element at the proximal end of the projection element is the same as a basis weight of a projection element at the distal end of the projection element.

20. The method of claim 12, wherein each projection element has a uniform density.

* * * * *